(12) United States Patent
Homyk et al.

(10) Patent No.: US 9,839,365 B1
(45) Date of Patent: Dec. 12, 2017

(54) APPLICATIONS OF VASCULATURE MAPPING USING LASER SPECKLE IMAGING

(71) Applicant: Verily Life Sciences LLC, Mountain View, CA (US)

(72) Inventors: Andrew Homyk, Belmont, CA (US); Jason Donald Thompson, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 217 days.

(21) Appl. No.: 14/551,480

(22) Filed: Nov. 24, 2014

(51) Int. Cl.
*A61B 5/1455* (2006.01)
*A61B 5/026* (2006.01)
*A61B 5/00* (2006.01)

(52) U.S. Cl.
CPC ........ *A61B 5/0261* (2013.01); *A61B 5/14551* (2013.01); *A61B 5/742* (2013.01)

(58) Field of Classification Search
CPC ............ A61B 5/14551; A61B 5/14552; A61B 5/6826; A61B 5/6838; A61B 5/1495
See application file for complete search history.

(56) References Cited

U.S. PATENT DOCUMENTS

| | | | |
|---|---|---|---|
| 7,113,817 B1 * | 9/2006 | Winchester, Jr. .... | A61B 3/1233 356/27 |
| 2005/0143662 A1 * | 6/2005 | Marchitto ............ | A61B 5/0066 600/473 |
| 2012/0065490 A1 | 3/2012 | Zharov et al. | |
| 2013/0184544 A1 | 7/2013 | Su et al. | |
| 2013/0190580 A1 * | 7/2013 | Baker, Jr. ............. | A61B 5/0059 600/323 |
| 2013/0324866 A1 | 12/2013 | Gladshtein | |
| 2014/0094663 A1 | 4/2014 | LeBoeuf et al. | |
| 2014/0357990 A1 * | 12/2014 | Wang ................... | A61B 5/0261 600/425 |

FOREIGN PATENT DOCUMENTS

WO 2013/030744 A1 3/2013

* cited by examiner

*Primary Examiner* — Eric Winakur
*Assistant Examiner* — Marjan Fardanesh
(74) *Attorney, Agent, or Firm* — Christensen O'Connor Johnson Kindness PLLC

(57) ABSTRACT

Systems are provided for detecting the flow of blood or other fluids in biological tissue by illuminating the biological tissue with a coherent light source and detecting time-varying patterns of constructive and destructive interference in light received from portions of the biological tissue by an imager. The movement of blood cells and other light-scattering elements in the biological tissue causes transient, short-duration changes in light emitted from portions of the biological tissue proximate to the moving blood cells or other scatterers. High-frequency sampling or other high-bandwidth processing of light intensities detected by an imager could be used to determine the flow of blood or other fluids at a plurality of points in the biological tissue, to detect and/or localize a tumor in the biological tissue, to determine the location, pattern, width, or other properties of vasculature in the biological tissue, or to provide information for some other application(s).

14 Claims, 9 Drawing Sheets

APPLICATIONS OF VASCULATURE MAPPING USING LASER SPECKLE IMAGING

BACKGROUND

Unless otherwise indicated herein, the materials described in this section are not prior art to the claims in this application and are not admitted to be prior art by inclusion in this section.

Illumination of a scattering environment (e.g., an environment containing rough surfaces or other scattering objects or features) by a source of coherent, monochromatic light (e.g., a laser) can result in light emitted (i.e., reflected, refracted, diffracted, or otherwise scattered) from the environment forming a speckle pattern. That is, constructive and destructive interference between coherent, monochromatic light that takes different paths through the scattering environment due to scattering by features of the environment, and that thus experiences different path lengths, can form a pattern of light and dark speckles across a surface (e.g., a planar array of light sensors). The speckle pattern can be related to the features of the scattering environment, such as the specific geometry of a rough surface and the locations, orientations, and properties of individual scattering objects (e.g., blood cells) in the environment).

SUMMARY

Some embodiments of the present disclosure provide a system including: (i) a light source, wherein the light source is configured to emit a beam of coherent illumination into a biological tissue; (ii) an imager configured to image a plurality of portions of the biological tissue, wherein the imager includes a plurality of light-sensitive elements and each light-sensitive element is configured to receive light from a respective portion of the biological tissue; and (iii) a controller operably coupled to the camera and light source, wherein the controller includes a computing device programmed to perform controller operations including: (a) operating the light source to emit a beam of coherent illumination into the biological tissue; (b) operating the imager to detect a plurality of time-varying patterns of constructive and destructive interference, wherein each time-varying pattern of constructive and destructive interference is in light received by a respective light-sensitive element from a respective portion of the biological tissue in response to the coherent illumination from the light source; and (c) determining a plurality of flow properties in the biological tissue based on the plurality of time-varying patterns of constructive and destructive interference detected by the imager.

Some embodiments of the present disclosure provide a system including: (i) a light source, wherein the light source is configured to emit a beam of coherent illumination into a biological tissue; (ii) an imager configured to image a plurality of portions of the biological tissue, wherein the imager is configured to receive light from a plurality of portions of the biological tissue; and (iii) a controller operably coupled to the camera and light source, wherein the controller includes a computing device programmed to perform controller operations including: (a) emitting a beam of coherent illumination into the biological tissue using the light source; (b) detecting, using the imager, a plurality of time-varying patterns of constructive and destructive interference, wherein each time-varying pattern of constructive and destructive interference is in light received from a respective portion of the biological tissue in response to coherent illumination from the light source; and (c) determining a map of vasculature within the biological tissue based on the plurality of time-varying patterns of constructive and destructive interference detected by the imager.

Some embodiments of the present disclosure provide a method including: (i) illuminating a biological tissue with a beam of coherent illumination; (ii) imaging light received from the biological tissue in response to the coherent illumination, wherein imaging light received from the biological tissue includes detecting a plurality of time-varying patterns of constructive and destructive interference, wherein each time-varying pattern of constructive and destructive interference is in light received by a respective light-sensitive element of an imager from a respective portion of the biological tissue in response to the coherent illumination from the light source; and (iii) determining a plurality of flow properties in the biological tissue based on the plurality of time-varying patterns of constructive and destructive interference detected by the imager.

Some embodiments of the present disclosure provide a system including: (i) means for illuminating a biological tissue with a beam of coherent illumination; (ii) means for imaging light received from the biological tissue in response to coherent illumination, wherein imaging light received from the biological tissue includes detecting a plurality of time-varying patterns of constructive and destructive interference, wherein each time-varying pattern of constructive and destructive interference is in light received by a respective light-sensitive element of the imaging means from a respective portion of the biological tissue in response to the coherent illumination from the light source; and (iii) means for determining a plurality of flow properties in the biological tissue based on the plurality of time-varying patterns of constructive and destructive interference detected by the imaging means.

These as well as other aspects, advantages, and alternatives, will become apparent to those of ordinary skill in the art by reading the following detailed description, with reference where appropriate to the accompanying drawings.

DETAILED DESCRIPTION

Figure 1:
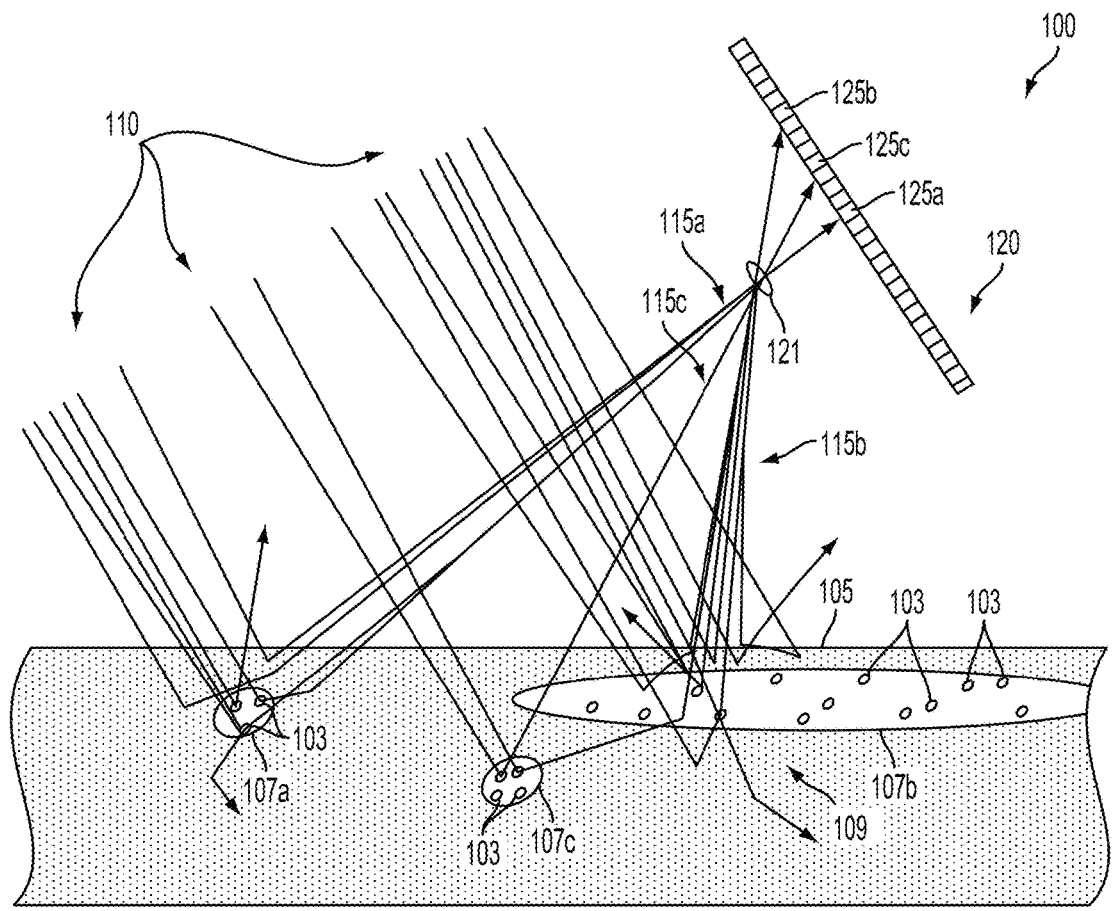
FIG. 1 is side partial cross-sectional view of an example system, while measuring fluid flow in biological tissue.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where detection of flow properties (e.g., of a map of flow properties across an area and/or within a volume) is desired. The environment may be any living or non-living body or a portion thereof, a gel, an emulsion, a fluid conduit, a fluid reservoir, etc. For example, one of skill in the art will recognize that the embodiments disclosed herein may be used to sense properties of fluid flow in a microfluidic system. Moreover, while the present disclosure describes embodiments for use in vivo, one of skill in the art will also recognize that in vitro applications are possible as well. Accordingly, the environment may also include a test tube or other vessel for holding a fluid.

I. OVERVIEW

A property of flow in an environment (e.g., a mean velocity of a fluid flow in an environment, a peak velocity of scatterers in an environment, a distribution of velocities of scatterers in an environment) can be detected by illuminating the environment using a beam of substantially coherent, monochromatic light emitted by a light source (e.g., a laser) and detecting a time-varying pattern of constructive and destructive interference in light emitted by the environment in response to the illumination. That is, scattering of the illumination by scattering elements in the environment (e.g., cells in blood, smoke particles in air) could cause constructive and destructive interference between illuminating light that takes different paths through the scattering environment, thus forming a pattern of light and dark speckles when projected on a surface (e.g., a focal surface of a camera or other imaging device). A plurality of light-sensitive elements could be disposed on the surface and configured to detect the intensity (or some other property) of light emitted by the environment in response to the illumination.

Changes in the detected level of intensity of the light received by each of the light-sensitive elements over time (i.e., a time-varying pattern of constructive and destructive interference in the light emitted by the environment) could be used to determine a plurality of flow properties in the environment. For example, the duration, rise time, fall time, and/or some other property of pulses, transitions, or other features of a time-varying intensity of light received by a particular light-sensitive element could be related to a flow property (e.g., a flow rate of blood cells) in or near a portion of the environment corresponding to the particular light-sensitive element. Flow properties could be determined for a plurality of points or regions in an environment to allow for a variety of applications, for example, to determine a flow map of fluid flows in the environment, to detect the presence, shape, width, pattern, or other information about vasculature in the environment, to detect a tumor or other target in the environment, or some other application(s).

The environment could be any environment that, when illuminated by a laser or other source of substantially coherent light, emits light having a pattern of constructive and destructive interference (e.g., a speckle pattern) related to the configuration of elements (e.g., scattering elements, blood cells) in the environment such that a change in the pattern of light can be related to a flow property of one or more regions of the environment (e.g., a velocity of flow of a liquid in the environment). The environment could include gases, liquids, gels, or other fluids. The environment can include a population of scattering agents, i.e., small particles or other objects or features that can move with a fluid flow and reflect, refract, diffract, or otherwise scatter light. In some examples, the environment could be a biological environment that includes blood cells, portions of vasculature, and other tissues. For example, the environment could be a biological tissue in a surgical environment that is subject to a surgical intervention, e.g., to an intervention that includes cutting, ablating, ligating, cauterizing, or otherwise manipulating or interacting with regions of the biological tissues according to an application.

Changes in the arrangement of scattering agents or other scattering features within the environment can cause a change in the pattern of light (i.e., the speckle pattern) emitted from the environment in response to coherent illumination. For example, displacement of scattering features (e.g., blood cells) disposed in a fluid (e.g., blood in a portion of vasculature, interstitial fluid in a tumor) due to flow of the fluid can cause a change in the pattern of emitted light that is related to the direction, velocity, or other properties of the fluid, the fluid flow, and/or the location and/or orientation of the scattering features. When intensity of light emitted from a particular region (e.g., from an area of the environment corresponding to the field of view of a light-sensitive element of a camera or other imager) is measured over time, time dependent features of the measured intensity (i.e., a waveform of the measured intensity) can be related to a flow property and/or other properties of the environment within and/or proximate to the particular region.

For example, movements of blood cells proximate to the particular region can cause the corresponding light-sensitive element to experience a 'speckle event', wherein the intensity of the light received by the light-sensitive element from the environment increases/decreases suddenly, followed by a sudden decrease/increase. Such a pulse in the intensity could take the form of a quasi-trapezoidal pulse, a raised-cosine pulse, or some other pulse shape. Further, one or more properties of the speckle event pulse (e.g., a rise time, a fall time, a pulse width, a pulse amplitude) could be related to a flow property (e.g., a velocity of an individual blood cell in a blood or interstitial fluid flow or a distribution of velocities of individual blood cells in a blood or interstitial fluid flow) of the environment. Other properties (e.g., a rate of change) of the measured intensity level over time could be related to flow properties of the environment. For example, an average intensity could be detected, over a period of time (e.g., during an exposure) by the light-sensitive element. Such a detected average intensity could be related to a frequency of speckle events or some other property of the particular region. Such a detected average intensity, a relationship between such average intensities measured across a region (e.g., a contrast value determined for a region based on detected average intensity values for the region, i.e., a spatial contrast), or some other detected property of one or more intensities or other detected properties of detected light from one or more portions of the environment could be used to determine flow properties of the environment.

In some examples, the intensity of the received light (as detected using one or more light-sensitive elements of an imager) could be sampled at a high rate by an analog-to-digital converter, and subsequent processing could be performed by a processor or other computational substrate, based on the sampled intensity information, to determine flow properties of the environment. In some examples, analog circuitry (e.g., operational amplifiers, filters, comparators, sample-and-holds, peak detectors, differentiators) could be included to perform some analog computation on the output of individual light-sensitive elements. For example, a rate of change (i.e., slope) of the output of a particular light-sensitive element could be computed using a differentiator, and the output of the differentiator could be passed to a peak detector, such that the output of the peak detector could be related to the velocity of the highest-velocity scattering feature to have caused a speckle event as measured by a light sensor during a specified period of time. An imager could include a plurality of such analog circuits connected to respective light-sensitive elements of the imager; additionally or alternatively, multiple light-sensitive elements could be multiplexed or otherwise connected to a single such analog circuit. Additional or alternative methods of using the outputs of light-sensitive elements to determine flow properties of an environment are anticipated.

In some embodiments, multiple light sources could be configured to emit beams of illumination having different wavelengths and/or from different angles or locations relative to an environment of interest and/or relative to light sensors to determine flow properties of the environment or according to an application. For example, first and second light sources could emit respective first and second beams of coherent light at respective first and second wavelengths into an environment, and one or more properties of lights emitted from the environment in response to the illumination could be used to determine and/or detect one or more properties of the environment. For example, a binding state of a fluorophore or chromophore, an oxygenation level of blood cells, or some other property of the environment could be determined based on the lights emitted from the environment. In some examples, an intensity, direction, and/or location of a beam of coherent light emitted into an environment could be controlled according to an application, for example, to optimize a dynamic range of one or more light-sensitive elements of an imager to allow for detection of flow properties of the environment. This could include controlling a direction or other property of a beam of coherent light emitted by a light source using one or more actuated optical elements. Additionally or alternatively, this could include operating a specified light source of a plurality of light sources to illuminate a corresponding specified region of the environment.

In some embodiments, the above described system may be implemented as a stationary measurement device that may be brought into contact or proximity with a target environment. For example the system could be configured to emit coherent light toward a biological tissue undergoing a surgical intervention, and to determine a plurality of flow properties of the biological tissue based on received light responsively emitted from the biological tissue. Such determined flow properties could be used to map vasculature in the biological tissue, to detect the presence and/or location of a tumor in the biological tissue, or to determine some other information about the biological tissue. Such information could be presented (e.g., via a display, via an augmented reality device, via a control console of a robotic surgical system) to a surgeon. Additionally or alternatively, such information could be used to operate an automated or semi-automated robotic surgical system (e.g., to inform the ablation of a tumor detected in the tissue while avoiding causing damage to vasculature in the tissue). In other embodiments, the above described system may be implemented to interrogate an environment that is not a part of a human body, e.g., an in vitro or other sample container, an outdoor environment, an animal body, or some other environment of interest that can scatter an emitted beam of coherent illumination in a manner related to flow properties of the environment.

It should be understood that the above embodiments, and other embodiments described herein, are provided for explanatory purposes, and are not intended to be limiting.

II. ILLUSTRATIONS OF FLOW PROPERTIES AND SCATTERING OF COHERENT LIGHT IN BIOLOGICAL TISSUES

Flow properties (e.g., flow rates at a plurality of locations) of fluid in an environment (e.g., blood in a portion of vasculature and/or interstitial space, a liquid, gel, emulsion, gas, or other flowing material in an industrial or other environment) can be detected by a variety of methods related to properties of the fluid and of the environment. In examples wherein the environment contains scatterers (i.e., particles that can scatter incident illumination and that can be affected by a fluid or other flow in the environment), flow properties of the environment could be detected and/or determined by illuminating the environment with coherent illumination and detecting a time- and/or space-dependence of a pattern, intensity, or other property of constructive and destructive interference in illumination scattered by the scatterers.

FIG. 1 is a cross-sectional view through biological tissue 105 illustrating the operation of an example system 100. In the example shown in FIG. 1, the system 100 includes a laser (not shown) configured to emit a beam of coherent illumination 110 into the biological tissue 105 including portions of subsurface vasculature 107a, 107b, 107c containing blood cells 103 (i.e., scatterers). The system 100 additionally includes an imager 120 comprising a plurality of light-sensitive elements (e.g., 125a, 125b, 125c) and an aperture 121 configured such that each light-sensitive element receives emitted light (e.g., 115a, 115b, 115c) from a respective portion of the biological tissue 105. For example, a first light-sensitive element 125a receives first emitted light 115a from a portion of the biological tissue 105 proximate to a first portion of vasculature 107a. The system 100 additionally includes a controller (not shown) configured to operate the laser and the imager 120 to determine a plurality of flow properties (e.g., flow rates in a plurality of locations within the biological tissue 105) of blood cells or other scattering elements in the biological tissue 105. The system 100 could include further elements, e.g., a housing within which the laser, imager 120, and/or controller could be disposed, a mount configured to mount the laser and imager 120 to an arm or to other elements of anatomy of a person or to some surgical equipment or system, or to some other elements.

Emitted light (e.g., 115a, 115b, 115c) from the biological tissue 105 could include patterns of constructive and destructive interference related to individual portions of the beam of coherent illumination 110 being scattered by different scattering (e.g., reflecting, refracting, diffracting) elements in the biological tissue 105 (e.g., cell walls, blood cells, cell elements, tissue boundaries, chromophores, fat globules, or other reflective elements/boundaries and/or discontinuities in refractive index). Thus, different portions of the coherent illumination 110 experience different path lengths between emission at the laser and reception at a light-sensitive element (e.g., 125a, 125b, 125c) of the light sensor 120. The different portions of the beam of coherent illumination 110 (having been scattered toward the light sensor in the form of the emitted light 115a, 115b, 115c) are thus out of phase and will constructively and/or destructively interfere with each other in a manner related to respective amplitudes and relative phases of the portions of the emitted light (e.g., 115a, 115b, 115c) to form a pattern of constructive and destructive interference at the light sensor 120 and/or at other locations in the vicinity of the system 100 and biological tissue 105.

As illustrated in FIG. 1, illumination 110 can be scattered multiple times before being emitted from or absorbed by the biological tissue 105. Such scattering can be caused by changes in refractive index or other scattering and/or reflective structures in the tissue, including cell walls, organelles within cells, artificial structures (e.g., nanoparticles) introduced into the tissue 105, or other elements of or within the biological tissue 105. As a result, light emitted from a particular portion of tissue may include light scattered from elements within the particular portion of tissue as well as light scattered by/within neighboring portions of tissue. Light emitted from the particular portion of tissue could be detected and used to determine information about the particular portion of tissue and/or portions of tissue neighboring the particular portion of tissue. For example, a time-varying pattern of constructive and destructive interference in light emitted from a particular portion of tissue could be detected and used to determine a time-varying state (e.g., velocity) of scattering agents (e.g., blood cells) in the particular portion of tissue and/or in portions of tissue neighboring the particular portion of tissue.

As an illustrative example, FIG. 1 shows emitted light 115b emitted from a particular portion 109 of the biological tissue 105 that includes a second portion of vasculature 107b. Some of the emitted light 115b comprises light that is scattered only by elements within the particular portion of biological tissue 109. Additionally, some of the emitted light 115b comprises light that is scattered outside of the particular portion of biological tissue 109. For example, some of the emitted light 115b is scattered by blood cells 103 or other scattering elements (e.g., cell walls, organelles) disposed within the third portion of vasculature 107c before being emitted from the particular portion of biological tissue 109 toward the imager 120 (e.g., as the emitted light 115b that is received by a corresponding light-sensitive element 125b). Thus, changes in the biological tissue 105 that occur outside of the particular portion of biological tissue 109 (e.g., movement of blood cells in a blood flow within the third portion of vasculature 107c) could be related to a time-varying pattern of constructive and destructive interference in the emitted light 115b that is received by the corresponding light-sensitive element 125b.

Time-varying patterns of constructive and destructive interference (e.g., speckle events, spatial contrast) in light emitted from a particular portion of biological tissue could be related to changing properties of the particular portion of biological tissue, or of neighboring portions of tissue. The relationship between the time-varying patterns in the emitted light and the changing properties of a portion of tissue could be related to a depth of the tissue, a distance between the tissue and a surface via which the light is emitted, a coherence length and/or wavelength of illumination applied to the biological tissue, or some other properties of the biological tissues, the illumination applied to the tissues, and/or an imager or other sensor(s) used to receive light responsively emitted from the tissues.

Thus, time-varying patterns of constructive and destructive interference in the emitted light (e.g., 115a, 115b, 115c) can be related to a configuration of elements of the biological tissue 105 (e.g., to the location of blood cells 103 in portions of subsurface vasculature 107a, 107b, 107c and/or interstitial spaces). The imager 120 detecting such time-varying patterns of constructive and destructive interference could include the imager 120 being configured and/or operated to detect any property or properties of emitted light (e.g., 125a, 125b, 125c) from the biological tissue 105 having a time dependence or other property that can be used to determine flow properties of blood or other fluids in the biological tissue 105. In some examples, this could include individual light-sensitive elements (e.g., 125a, 125b, 125c) of the imager 120 being configured to detect the intensity and/or some other property of the emitted light 117 at a plurality of points in time. For example, the intensity could be detected at a sufficiently high rate to detect the presence or other properties of individual speckle events or other short-duration features of the detected intensity.

Additionally or alternatively, information about time-varying patterns of constructive and destructive interference in the received light could be detected by filtering, integrating, or otherwise performing some analog operations on light received by individual light-sensitive elements of the imager 120. For example, an average intensity of the received light during a specified period of time (e.g., during an exposure having a specified duration) could be detected and used to determine flow properties in the biological tissue 105. In another example, a power of a detected intensity or property of the received light within a specified range of frequencies could be determined by filtering the detected property (e.g., filtering by analog electrical circuits and/or by sampling the detected property at a sufficiently high rate and operating a controller to apply the filter computationally) and relating the determined power to flow properties in the biological tissue 105. Further, such detected time-varying patterns corresponding to a plurality of different portions of tissue (e.g., detected using a corresponding plurality of light-sensitive elements of the imager 120) could be combined to determine flow properties of the biological tissue 105 (e.g., by determining a spatial contrast in images of the biological tissue 105 detected using the imager 120).

In some examples, the imager 120 could be a camera (i.e., could include aperture (e.g., 121), an array of light-sensitive elements (e.g., 125a, 125b, 125c), and/or optics) and detecting the time-varying patterns of constructive and destructive interference could include detecting the intensity of the emitted light (e.g., 115a, 115b, 115c) that is received by the camera from various respective angles relative to the camera. Alternatively, the imager 120 could include a plurality of light-sensitive elements configured to receive light from respective portions of biological tissue by other means. In some examples, the individual light-sensitive elements could include baffles, coded apertures, diffraction gratings, angle-sensitive pixels (e.g., pixels of a planar Fourier capture array), or other elements configured such that individual light-sensitive elements receive light from a specified portion of tissue (e.g., at a specified angle(s) and/or specified location(s) relative to the light sensitive-element). Other configurations and operations of one or more imagers (e.g., 120) to detect the patterns of constructive and destructive interference in light emitted are anticipated.

Detecting time-varying patterns of constructive and destructive interference in light emitted from the biological environment 105 (e.g., 115a, 115b, 115c) could include detecting a variety of properties of the patterns of constructive and destructive interference and/or of received light containing such time-varying patterns. Detected properties of the patterns of constructive and destructive interference and/or received light could include the intensity, wavelength, spectrum, degree of polarization, direction of polarization, or some other property of received light emitted from a specified location(s) of the biological tissue 105 and/or from a particular direction relative to a light sensitive element. Detected properties of the patterns of constructive and destructive interference could include properties of an image formed by the detected patterns of constructive and destructive interference (e.g., an image detected using the imager 120, an array of light-sensitive elements on a surface, or some other image-detecting apparatus); for example, a contrast ratio, a speckle location, a speckle size, a number of speckles, a speckle shape, an overall pattern width, or some other property or properties.

Figure 2:
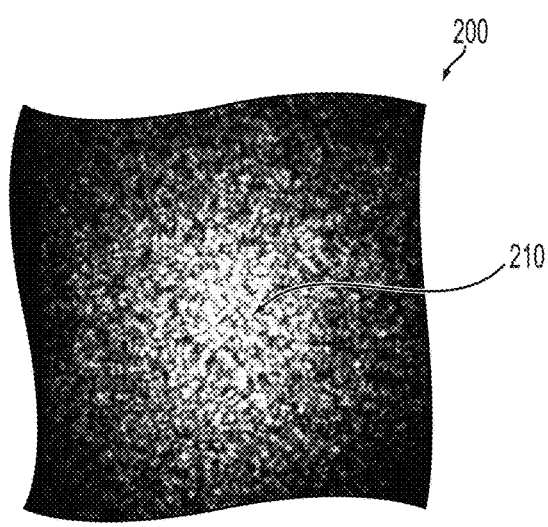
FIG. 2 is an example image of a speckle pattern emitted by a scattering medium that is illuminated by coherent light.

FIG. 2 illustrates an example speckle image 200 that could be generated on an imaging surface (e.g., a surface of the imager 120 on which light-sensitive elements, e.g., 125a, 125b, 125c, are disposed) in response to illumination of a scattering environment (e.g., the biological tissue 105, portions of subsurface vasculature 107a, 107b, 107c, blood cells 103) by light emitted from the environment (e.g., 115a, 115b, 115c) in response to a beam of coherent illumination (e.g., a beam 110 emitted by a laser). The speckle image 200 includes a plurality of speckles 210 corresponding to where (e.g., the locations of one or more particular pixels) the constructive and destructive sum of the light impinging on a corresponding region of the imaging surface results in an overall higher level of light intensity than in other regions of the speckle image 200.

Properties of the patterns of constructive and destructive interference that result in the speckle image 200 are related to properties of the scattering environment (e.g., location of scattering elements in the environment, refractive index of elements of the environment), properties of the illuminating beam of coherent illumination (e.g., a wavelength, a spectral line width, an intensity, a coherence length, a beam width, a beam polarization), and of the imaging surface (and/or of apertures, optics, or other elements of an imager 120 comprising such a surface) on which the speckle image 200 is formed (e.g., the location of the imaging surface relative to the beam of coherent illumination and the environment). Thus, time-dependent changes in the configuration of the environment (e.g., movement of scatterers in a fluid flow in the environment) could result in a time-dependent change in the patterns of constructive and destructive interference in the light emitted by the environment that could further result in a time-dependent change in the imaged speckle pattern 200. That is, the location, number, size, shape, intensity, or other properties of speckles 210 or other features of the speckle pattern 200 could change in a time-dependent manner related to a change in the environment and/or a change in the location of the imaging surface and/or source of the beam of coherent illumination relation to the environment.

The patterns of constructive and destructive interference represented by the speckle image 200 could be related to reflection, refraction, diffraction, scattering, absorption, or other interactions between a beam of coherent light illuminating an environment and elements of the environment. For example, interfaces between regions of the environment having different indices of refraction (e.g., at a cell wall, at a wall of an organelle or other cellular contents, at the wall of a portion of vasculature, at the surface of a bone, at the surface of a muscle, at a skin surface, at some other interface in a biological or other environment) can cause scattering, refraction, reflection, and/or other interactions with light. Other elements of an environment (e.g., metallic and/or semiconductive particles, surfaces, or other elements) could cause reflection, scattering, and/or other interactions with illuminating light in a manner related to the patterns of constructive and destructive interference represented by the speckle image 200.

FIGS. 3A-3E illustrate the operation of an example system 300 that could be operated to determine flow properties (e.g., flow rates within a volume) of blood in a portion of subsurface vasculature 307 and/or other portions of tissue in an arm 305. The system 300 includes a laser 310 configured to emit a beam of coherent illumination (a portion of which is illustrated as illumination 315) into tissue of the arm 305 that includes the portion of subsurface vasculature 307 and blood cells (e.g., illustrative blood cell 309) contained in the portion of subsurface vasculature 307 that move along with blood in the portion of subsurface vasculature 307. The system 300 additionally includes an imager that includes an aperture 321 and a particular light-sensitive element 320 configured to detect a time-varying pattern of constructive and destructive interference in a portion of the beam of coherent illumination 315 that is scattered by tissue of the arm 305 and that is emitted as an emitted light 321 toward the imager such that the emitted light 321 is received by the particular light-sensitive element 320. The imager could additionally include a plurality of additional light-sensitive elements (e.g., formed as part of a CCD, CMOS active-pixel sensor (APS) array, or other light-sensitive structure with the particular light-sensitive element 320) configured to receive light from a plurality of respective locations of the arm 305 and/or from respective angles relative to the imager. The system 300 additionally includes a controller (not shown) configured to operate the laser 310 and the imager to determine flow properties (e.g., a flow rate) of blood in the portion of subsurface vasculature 307 and/or other portions of tissue of the arm 305. The system 300 could include further elements, e.g., a housing within which the laser 310, imager, and/or controller could be disposed, a mount configured to mount the laser 310 and light sensor 320 to the arm 305, or some other elements.

Figure 3A:
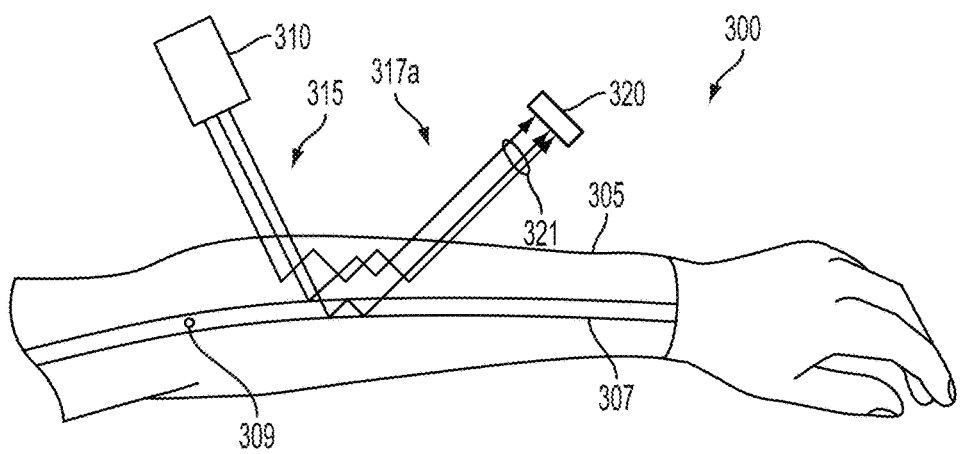
FIG. 3A is side partial cross-sectional view of an example system, while measuring blood flow in a human arm.
Figure 3B:
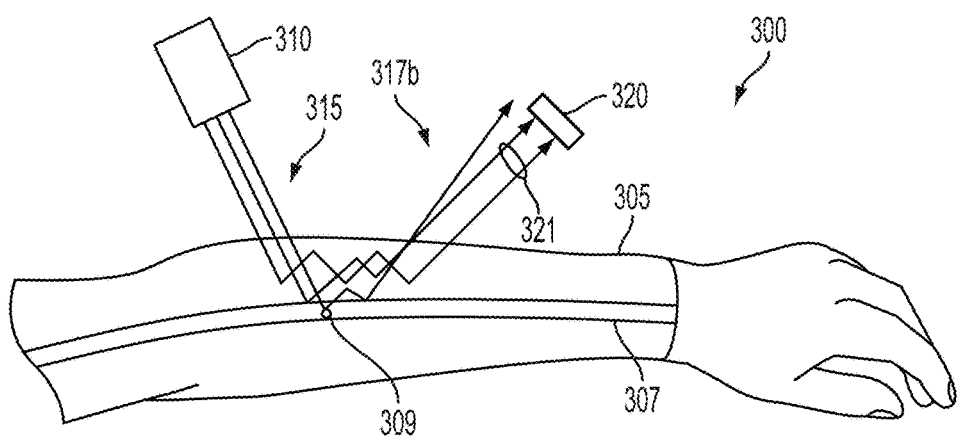
FIG. 3B is side partial cross-sectional view of the example system illustrated in FIG. 3A, while measuring blood flow in a human arm.
Figure 3C:
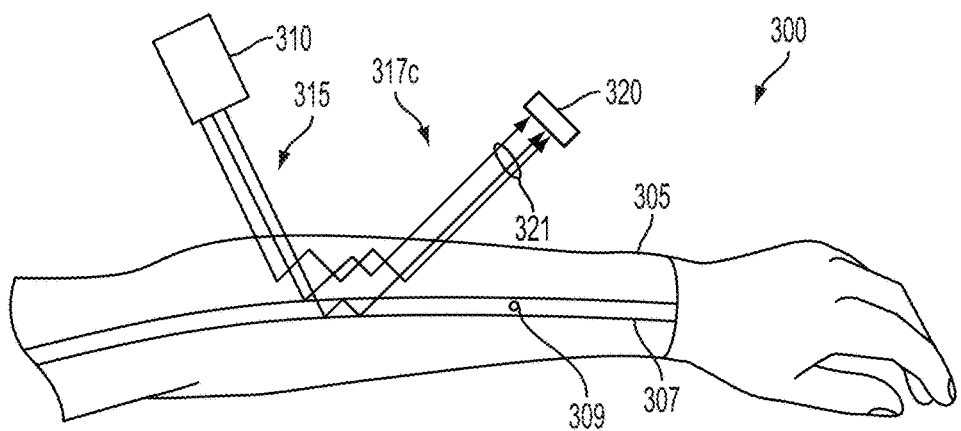
FIG. 3C is side partial cross-sectional view of the example system illustrated in FIG. 3A, while measuring blood flow in a human arm.
Figure 3D:
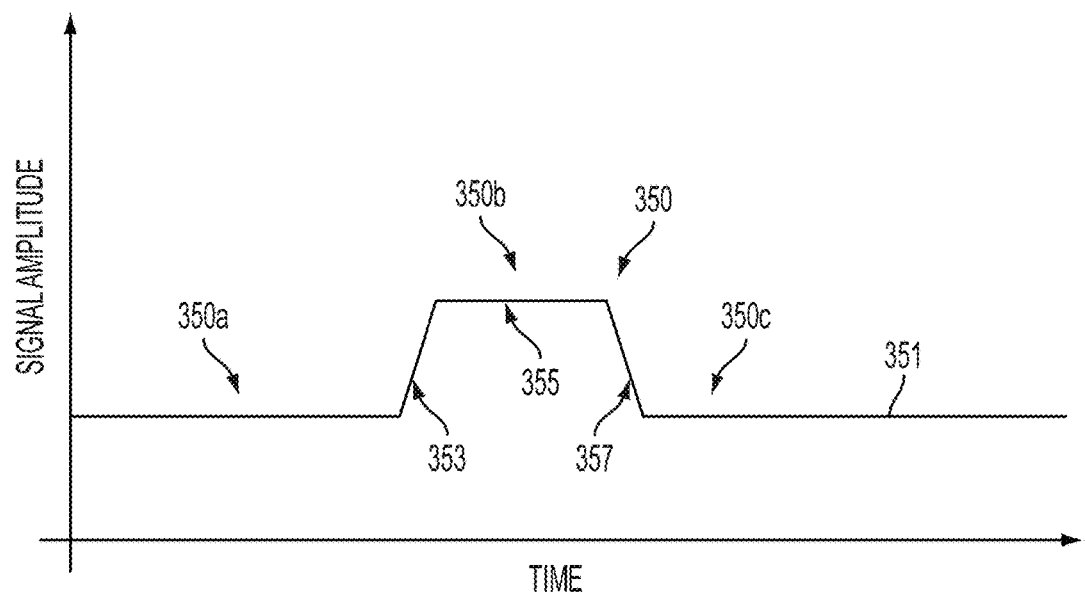
FIG. 3D is an example output generated by the example system illustrated in FIGS. 3A-3C.

To illustrate the operation of the system 300, the movement of an illustrative blood cell 309 due to blood flow in the portion of subsurface vasculature 307 is illustrated in FIGS. 3A-3C and the corresponding time-dependent changes of the pattern of constructive and destructive interference detected by the particular light-sensitive element 320. Specifically, FIG. 3D illustrates an example detected light intensity waveform 351 corresponding to the intensity of the time-varying pattern of constructive and destructive interference in light emitted from a particular portion of the arm 305 as detected by the particular light-sensitive element 320.

FIG. 3A illustrates the system 330 and arm 307 during a first period of time. The illustrative blood cell 309 is in an upstream region of the portion of subsurface vasculature 307 that is substantially outside of a region illuminated by the illustrated coherent illumination 315. As a result, the particular light-sensitive element 320 detects a first light intensity 350a related to a pattern of constructive and destructive interference in first emitted light 317a.

FIG. 3B illustrates the system 330 and arm 307 during a second period of time. The illustrative blood cell 309 is moved downstream due to blood flow into the region of the portion of subsurface vasculature 307 that is illuminated by the illustrated coherent illumination 315 and thus acts to scatter the illustrated coherent illumination 315. As a result, the particular light-sensitive element 320 detects a second light intensity 350b related to a pattern of constructive and destructive interference in second emitted light 317b that is substantially different from the pattern of constructive and destructive interference in first emitted light 317a.

FIG. 3C illustrates the system 330 and arm 307 during a third period of time. The illustrative blood cell 309 is moved downstream due to blood flow into a downstream region of the portion of subsurface vasculature 307 that is substantially outside of the region illuminated by the illustrated coherent illumination 315. As a result, the particular light-sensitive element 320 detects a third light intensity 350c related to a pattern of constructive and destructive interference in third emitted light 317c that is substantially similar to the pattern of constructive and destructive interference in first emitted light 317a.

The movement of the illustrative blood cell 309 through the portion of subsurface vasculature 305 during and between the first, second, and third periods of time (as illustrated in FIGS. 3A-C, respectively) results in the particular light-sensitive element 320 detecting an illustrative speckle event 350 in the detected light intensity waveform 351. The illustrative speckle event 350 is a trapezoidal pulse that includes a rising edge 353, a plateau 355, and a falling edge 357. One or more of these waveform elements could be related to the speed of the illustrative blood cell 309 and thus to a flow property in the biological tissues of the arm 305 (e.g., of the blood in the portion of subsurface vasculature 307). In some examples, a time property (e.g., a rise time of the rising edge 353, a duration of the plateau 355, a fall time of the falling edge 357) of the speckle event 350 could be related to a speed of the illustrative blood cell 309. For example, the rate of increase in intensity during the rising edge 353 could correspond to the velocity of the illustrative blood cell 309 such that higher rates correspond to higher velocities.

Note that the movement of the illustrative blood cell 309 and the corresponding detected light intensity waveform 351 are meant as illustrative examples. A portion of subsurface vasculature could include many blood cells having respective different velocities related to the movement of blood in the portion of subsurface vasculature. Further, the movement of an individual blood cell through a region of subsurface vasculature illuminated by a coherent light source could result in no speckle event, multiple speckle events, or some other feature(s) to be present in a detected light intensity waveform or other detected signal related to the pattern of constructive and destructive interference in a portion of a beam of coherent illumination that is scattered the environment including the portion of subsurface vasculature and blood cell(s)) and that is emitted as an emitted light toward a light sensor. Further, note that, due to multiple scattering of light in biological tissues of the arm 305, properties (e.g., speckle events) of a detected time-varying pattern of constructive and destructive interference could be due to flow properties in portions of biological tissue proximate to the region illuminated by the illustrated coherent illumination 315 and/or due to flow properties in neighboring portions of biological tissue (e.g., regions illuminated by other portions of a beam of coherent illumination emitted by the laser 310).

Figure 3E:
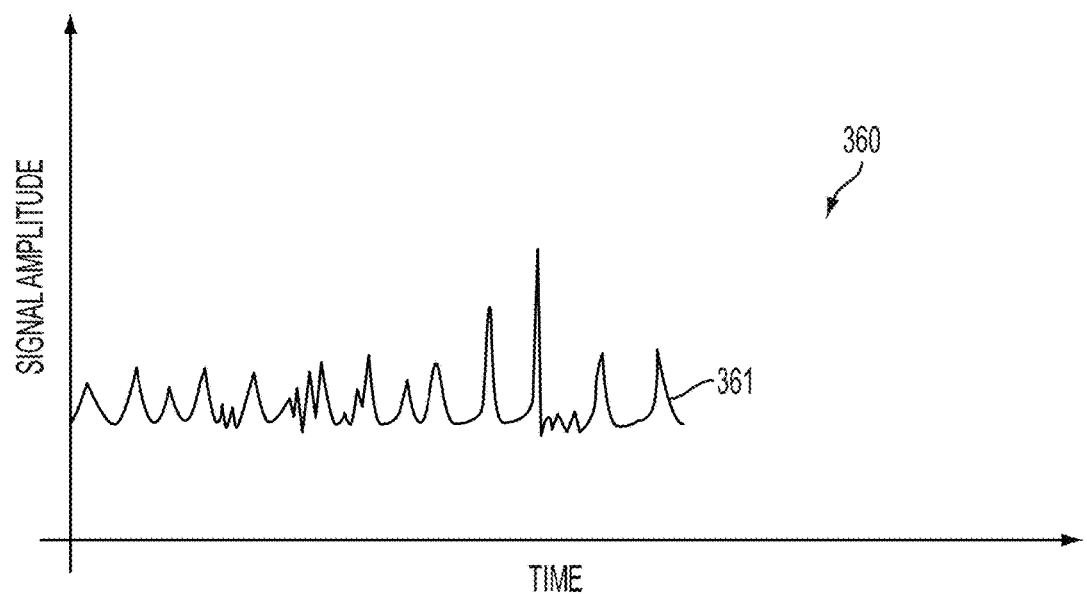
FIG. 3E is an example output generated by the example system illustrated in FIGS. 3A-3C.

FIG. 3E shows an example detected light intensity waveform 361 that could be detected using the system 300 when a plurality of blood cells and other scatterers are being moved in a flow of blood or other fluids in the arm 305. The detected light intensity waveform 361 includes a plurality of speckle events having respective shapes, durations, amplitudes, rise/fall times, and/or other properties. The system 300 could include electronics (e.g., amplifiers, filters, comparators, envelope detectors, slope detectors, differentiators, peak detectors, ADCs, microprocessors, microcontrollers) configured to determine one or more flow properties in biological tissue of the arm 305 (e.g., of the blood in the portion of subsurface vasculature 307) based on the detected light intensity waveform 361. For example, the electronics could be configured to detect a rise time of individual speckle events in the detected light intensity waveform 361 and to determine a corresponding blood cell velocity. The electronics could be further configured to determine a distribution of velocities of individual blood cells in the blood or other fluid, a mean flow rate of the blood or other fluid, and/or some other flow property of the blood or other fluid in the biological tissues of the arm 305.

Determined flow properties in an environment (e.g., of blood at one or more points within a portion of subsurface vasculature and/or at other locations in a biological tissue) could be any properties or physical parameters relating to a flow of a fluid within the environment. In some examples, determined flow properties could include the velocity, direction, acceleration, or other information about the movement of individual particles (e.g., blood cells or other scatterers) or groups of particles within the environment. For example, a system could determine the velocity of individual particles in the environment based on a detected temporal property of speckle events or other features of a detected waveform that is related to time-varying patterns of constructive and destructive interference in light emitted by the environment in response to illumination by a beam of coherent light. In some examples, determined flow properties could include properties describing a bulk flow of fluid, e.g., a flow rate, a mean flow velocity, a mean flow speed, a mass flow rate, or some other property of a fluid flow in an environment.

In some examples, the detected flow properties could correspond to respective portions (e.g., sub-regions, voxels) of an environment, e.g., blood cells in a particular volume of biological tissue (e.g., a portion of vasculature, a portion of a vein, a portion of an artery, a portion of a capillary bed) or other portion of anatomy. The location of the specified region could be related to the configuration of the system (e.g., the location and direction of a laser, the location and direction of sensitivity of a light sensor). For example, a laser of the system could be configured to emit a beam of coherent illumination in a specified direction relative to the laser, and an imager could be configured to detect a property of light received from a plurality of specified directions relative to the imager (e.g., relative to an aperture of the imager), such that the determined flow properties are flow properties of fluid proximate to respective intersections of the beam of coherent illumination and vectors extending from the imager in respective specified directions relative to the imager.

The laser 310 could be configured in a variety of ways and include a variety of elements such that the emitted beam of coherent illumination (e.g., illustrated portion of coherent illumination 315) has one or more specified properties according to an application. The beam of coherent illumination could have a specified wavelength. In some examples, the wavelength of the beam of coherent illumination could be specified such that it could penetrate an environment of interest, be scattered by scatterers in a fluid flow(s) in the environment of interest, or according to some other considerations. For example, the environment could include portions of vasculature within a portion of human anatomy (e.g., within a portion of tissue targeted for a surgical intervention), the determined flow properties could be flow properties of blood at a plurality of location within the portion of human anatomy, and the wavelength of the beam of coherent illumination could be between approximately 400 nanometers and approximately 1000 nanometers. In some examples, the wavelength of the beam of coherent illumination could be specified relative to a characteristic size or other property of scatterers (e.g., blood cells, cavitation bubbles, natural and/or artificial particles, bubbles or gas or other material having dissimilar optical properties to a surrounding fluid medium) such that the scatterers could scatter the beam of coherent illumination and cause the environment to emit light having time-varying patterns of constructive and destructive interference related to the configuration of the environment and/or scatterers (e.g., related to motion of the scatterers within fluid flows in an environment). The wavelength of the beam of coherent illumination could be within a near-infrared (NIR) transparency window of biological tissue (e.g., between approximately 780 and approximately 810 nanometers).

In some examples, the beam of coherent illumination could have a coherence length that is greater than some minimum coherence length (e.g., greater than 1 millimeter) that is related to scattering properties of elements of the environment (e.g., skin cells, connective tissue, portions of subsurface vasculature, blood cells, and other elements of biological tissues of a portion of human anatomy). The specified minimum coherence length could be related to a spacing of scatterers or other optical features (e.g., reflecting, refracting, and/or diffracting interfaces between regions having different indices of refraction, metallic and/or semi-conductive elements) in the environment such that one or more properties of time-varying patterns of constructive and destructive interference can be detected and used to a flow properties in the environment. Additionally or alternatively, the specified minimum coherence length could be related to a range of expected path lengths of scattered light through the environment. Further, the laser 310 could include a volume holographic grating, a monochromator, a Lyot filter, a Bragg reflector, a dielectric mirror, or some other element(s) configured to increase a coherence length of and/or decrease a spectral line width of the beam of coherent illumination. Such elements could be disposed on a discrete laser (e.g., a volume holographic grating could be disposed in the path of the beam of a laser) and/or could be incorporated into one or more elements of the laser 310 (e.g., mirrors, lenses, gain media, frequency doublers, or other elements of the laser 310 could be configured such that they had properties of one or more of the listed additional elements).

The laser 310 could be selected from a wide variety of lasers according to an application. The laser 310 could include a gas laser, a chemical laser, a dye laser, a metal-vapor laser, a solid-state laser, a semiconductor laser, or any other type of laser configured to produce a beam of coherent illumination having one or more specified properties (e.g., wavelength, spectral line width, coherence length, beam width, beam dispersion) such that the laser could illuminate an environment of interest (e.g., a portion of subsurface vasculature 307, tissues undergoing a surgical intervention) that contains light-scattering elements (e.g., blood cells, human tissue) such that the environment of interest responsively emits light having time-varying patterns of constructive and destructive interference that have one or more time-dependent properties that can be detected and used to determine flow properties (e.g., a flow rate of blood within a particular portion) of the environment. In some applications, the system 300 could be a wearable device and the laser 310 could be configured to satisfy limited power and space requirements of the wearable device such that the system 300 could be battery-powered and could be comfortably worn by a wearer (e.g., worn around a wrist of the wearer). The system 300 could be configured to be operated in a surgical environment (e.g., in connection with a variety of additional surgical instruments and/or imaging devices) and one or more elements of the system 300 could be configured to perform some additional function(s). For example, the laser 310 could additionally be configured to ablate biological tissue (e.g., by producing a beam of illumination of sufficient power to vaporize, cauterize, coagulate, ablate, or otherwise irreversibly alter biological tissue) and/or to control a direction of the emitted beam of coherent illumination (e.g., by being optically coupled to one or more actuated mirrors or other actuated elements).

In some examples, the laser 310 could be a small laser diode, e.g., a VCSEL, a double heterostructure laser, a quantum well laser, or some other structure of semiconductor laser incorporating gallium nitride, indium gallium nitride, aluminum gallium indium phosphide, aluminum gallium arsenide, indium gallium arsenide phosphide, lead salt, or some other material or combination of materials as a gain medium. In some examples, the laser 310 could include frequency doublers, optics, collimators, or some other elements according to an application. In some examples, the laser 310 could be incorporated into other elements of the system 300. For example, the laser 310 could be wire-bonded, soldered, or otherwise electronically and/or mechanically coupled to a circuit board or other element(s) of the system, 300. Additionally or alternatively, the laser 310 or elements thereof could be incorporated into a single semiconductor device (e.g., wafer or chip) with other components (e.g., a laser power supply, a microcontroller). Further, the laser 310 could be configured to control the direction of the beam of coherent illumination 315 (e.g., by including servos, motors, piezo elements, or other actuators configured to translate and/or rotate the laser and/or optics or other elements thereof) to enable detection of flow properties in specified sub-regions of the arm 305 by directing the beam of coherent illumination toward the different specified sub-regions of the arm 305.

In some examples, the system 300 could include more than one laser. Individual lasers of the more than one laser could have respective specified properties (e.g., locations, angles and/or locations of emitted beams of coherent illumination, wavelengths, coherence lengths, polarizations) according to an application. More than one laser could be provided to allow for detection of a flow properties in more than one region of the arm 305 (e.g., portions of tissue at multiple depths other and/or locations in the arm 305). In some embodiments, the system 300 could include a spatially distributed array of lasers configured such that individual lasers of the array emit beams of coherent illumination into respective individual sub-regions (e.g., overlapping or non-overlapping portions of tissue) of the arm 305. Such an array of lasers could be operated to determine a flow properties of the respective individual sub-regions of the arm 305 (e.g., to determine a flow map within the arm 305, to determine a location, shape or other property of vasculature in the arm 305, or according to some other application). More than one laser could be provided to enable higher-accuracy or otherwise improved detection of a flow property of blood, interstitial fluid, or some other fluid (e.g., by providing a redundant source of coherent illumination, by allowing illumination of a portion of biological tissue from multiple angles, by providing multiple wavelengths of illumination for detection).

More than one laser could be provided to enable measurement of more than one set and/or type of flow properties. For example, a first laser could emit a beam having a first wavelength that is preferentially scattered by a first population of scatterers in the environment (e.g., portion of subsurface vasculature, capillary bed) and a second laser could emit a beam having a second wavelength that is preferentially scattered by a second population of scatterers in the environment such that the first and second lasers could be operated, in combination with one or more imagers, to determine first flow properties in the environment related to movement of the first scatterers and second flow properties in the environment related to movement of the second scatterers. Additionally or alternatively, the first and second lasers could be configured to illuminate tissues at different depths beneath a surface, tissues at different locations in the environment, tissues having different absorbance and/or scattering properties, or according to some other difference.

Further, the use of multiple lasers to illuminate multiple portions of a biological tissue could allow for detection of flow properties in the multiple portions of the biological tissue by a reduced set of light-sensitive elements (e.g., by a single light-sensitive element). For example, the imager could include a single light-sensitive element (or a small set of light-sensitive elements) configured to receive light from a plurality of portions of a biological tissue, and one or more lasers could illuminate the plurality of portions of the biological tissue during respective periods of time. A plurality of time-varying patterns of constructive and destructive interference in light detected by the single light-sensitive element during respective periods of time could be used to determine flow properties in the biological tissue. One or more lasers illuminating a plurality of portions of the biological tissue could include operating a plurality of lasers configured to emit beams of coherent illumination toward respective portions of the biological tissue. Additionally or alternatively, one or more lasers could be configured to control a direction and/or location of an emitted beam of illumination to illuminate specified portions of the biological tissue (e.g., by being coupled to one or more actuated mirrors or by being otherwise configured to control a direction of an emitted beam of coherent illumination).

The imager (including particular light-sensitive element 320) could include any variety of light-detecting apparatus configured to detect time-varying patterns of constructive and destructive interference in light that is emitted by an environment (e.g., 305, 307) and that is related to the configuration of the environment and/or scatterers therein. The imager (including, e.g., particular light-sensitive element 320) could include one or more photodetectors, photodiodes, phototransistors, CCDs, active pixel sensors, angle-sensitive pixels, photoresistors, or other light-sensitive elements. The particular light-sensitive element 320 and/or other light-sensitive elements of the imager could be configured to detect an intensity, a wavelength, a spectrum, a degree of polarization, a direction of polarization, or some other property of light emitted by the environment and received at one or more locations on or within the imager. For example, light-sensitive elements of the imager could be configured to detect the intensity of light received from respective specified regions of the arm 305 that are received from respective directions relative to the imager. In some examples, the imager could comprise a camera (i.e., including, e.g., aperture 321, a plurality of particular light-sensitive elements 320, and/or optics).

Note that the imager being configured as a camera (that is, including an aperture 321, one or more light-sensitive elements 320, and/or other optical elements configured such that individual light-sensitive elements receive light from respective directions relative to the imager) is meant as a non-limiting example. In other examples, the imager could include a plurality of light-sensitive elements configured to receive light from respective portions of biological tissue by other means. In some examples, the individual light-sensitive elements could include baffles, coded apertures, diffraction gratings, angle-sensitive pixels (e.g., pixels of a planar Fourier capture array), or other elements configured such that individual light-sensitive elements receive light from a specified portion of tissue (e.g., at a specified angle(s) and/or specified location(s) relative to the light sensitive-element). Other configurations and operations of one or more imagers to detect the patterns of constructive and destructive interference in light emitted are anticipated.

The imager and/or light-sensitive elements thereof (e.g., 320) could include a variety of components according to an application. The imager could include lenses, polarization filters, color filters, apertures, mirrors, diffraction gratings, liquid crystal elements, baffles, or other optical elements to affect the light received by the imager and/or by particular light-sensitive elements thereof. In some examples, the imager could include a color filter configured to substantially block light having wavelengths different from a wavelength of light emitted by the laser 310. In some examples, the size of specified regions from which individual light-sensitive elements of the imager receive emitted light could be specified such that a bandwidth or other time-dependent property of a signal produced and/or detected by light-sensitive elements of the imager (e.g., a rate of speckle events detected by light-sensitive elements of the imager) is within some specified limit(s). For example, the specified region could be a region of biological tissue having a diameter or other characteristic size between approximately 100 microns and approximately 1 millimeter.

Note that the example speckle event 350 and other features of the example detected light intensity waveform 361 illustrated in FIGS. 3D and 3E, respectively, are meant as illustrative examples of signals related to time-varying patterns of constructive and destructive interference in light emitted from an environment of interest that could be used to determine flow properties in the environment. Rise times, rise rates, pulse widths, fall times, fall rates, and other temporal features of such detected signals are non-limiting examples of time-dependent waveform features that could be used to determine flow properties in an environment. Additionally or alternatively, an envelope, a spectrum, a derivative, a power in one or more frequency bands, a speckle or other event rate, an autocorrelation, or some other time-dependent variable or variables related to such detected signals could be used to determine flow properties in an environment.

In examples wherein multiple time-varying patterns of constructive and destructive interference in emitted light are detected, additional or alternate time-dependent methods and/or derived variables could be used to determine flow properties in an environment based on the multiple detected time-varying patterns. For example, where the imager includes a plurality of light-sensitive elements (e.g., a rectangular array of photodetectors arranged on a surface), one or more properties of an image generated by the imager could be used to determine flow properties in the environment. For example, a contrast level, a spatial correlation, a number of speckles in the image, a shape of speckles in the image, a change over time (e.g., a displacement, a change in size and/or shape) of speckles in the image, or some other property of an image generated by the imager could be determined and used to determine flow properties in the environment. Further, other image processing methods (e.g., optic flow detection) could be applied to the image before using the image to determine flow properties (e.g., to compensate for relative motion of the system 300, to compensate for nonlinearities and/or non-uniformities in the response of light-sensitive elements of the imager) and/or to determine flow properties directly (e.g., to determine a contrast map based on the image, and further to determine the flow properties based on the contrast map).

Determining flow properties in the environment could include sampling an output of the particular light-sensitive element 320 and/or some other light-sensitive elements of the imager (e.g., detected light intensities at a plurality of specified locations) at a sufficiently high frequency to determine and/or detect information in the output(s) (i.e., to detect the output(s) at a plurality of respective points in time) that is related to the flow properties. For example, a controller or other elements of the system 300 could operate a high-speed analog-to-digital converter (ADC) of the system 300 to sample an output (e.g., a voltage, a current) of the particular light-sensitive element 320 at a specified high rate (e.g., one megahertz) to detect features of individual speckle events in the output that have one or more properties (e.g., a pulse width, a rise time, a rise rate) related to flow properties of blood interstitial fluid, or other fluids in biological tissues of the arm 305. The specified high rate of sampling could be related to the duration, frequency, or some other temporal property of the output (e.g., an expected minimum duration of speckle events). For example, a speckle event could be expected to last approximately 1 microsecond, so the specified sample rate could be sufficiently in excess of 1 megahertz to resolve features of interest (e.g., a rising edge, a plateau, a falling edge) of individual speckle events.

Additionally or alternatively, the system 300 could include analog frontend circuitry configured to filter, decimate, quantize, or otherwise alter and/or perform other analog operations or computations on the output(s) of light-sensitive elements (e.g., 320) of the imager to produce an output electronic signal that is related to flow properties in the environment (e.g., a flow property in the portion of subsurface vasculature 307). This output electronic signal could then be used (e.g., sampled by an ADC of a microcontroller) to determine the flow properties. In examples wherein the imager has a plurality of electronic outputs (e.g., a plurality of voltage outputs relating to the intensity of light detected by a plurality of light-sensitive elements), the system 300 could include a plurality of such analog frontend circuits configured to receive respective outputs from respective light-sensitive elements of the imager and to output respective electronic signals related to the respective received sensor output signals. Additionally or alternatively, the system 300 could include fewer instances of such analog frontend circuitry, and the outputs of respective light sensitive elements could be electronically multiplexed such that the fewer instances of the analog frontend circuitry could be operated in combination with the outputs of the respective light-sensitive elements.

Analog frontend circuitry as described above could include a variety of components configured in a variety of ways to generate output electronic signals having a variety of properties related to flow properties in the environment. In one example, a rate of change of the output signal of the particular light-sensitive element 320 (e.g., a rise rate of rising edges of speckle events) could be related to the velocity of a corresponding scatterer in the environment. The analog frontend circuitry could include a differentiator configured to output a signal related to a rate of change of the output signal of the particular light-sensitive element 320. The differentiator could be passive (e.g., an RC and/or RL filter circuit), active (e.g., an op-amp configured with capacitors, resistors, and/or other elements as a differentiator), or some combination thereof. Further, the differentiator could be configured to output a signal that is related to the rate of change of the output signal of the particular light-sensitive element 320; for example, the differentiator could output a low-passed, rectified, or otherwise altered version of the rate of change of the output signal of the particular light-sensitive element 320. The analog frontend circuitry could additionally include a peak detector configured to output a signal related to the maximum value of the signal output by the differentiator during a specified previous time period. The peak detector could include passive and active components configured in a variety of ways. In some examples, the peak detector could include an op-amp, a rectifier, and a capacitor configured to output a signal equal to the maximum value of the input to the peak detector in the past. This variety of peak detector could additionally include a reset electronic switch that could be operated to reset the peak detector, allowing the peak detector to output a signal equal to the maximum value of the input to the peak detector during a previous time period specified by the operation of the electronic switch. Additionally or alternatively, the peak detector could include a lossy integrator. The output of the peak detector could form the output of the analog frontend circuitry, and could be used to determine flow properties in the environment (e.g., by sampling the output using an ADC at one or more points in time and operating a microcontroller based on the digital output(s) of the ADC).

Additional or alternative analog and/or digital components and/or combinations of such with circuitry described herein could be configured and/or operated to enable determination of flow properties in an environment based on signals output from the imager (e.g., from the particular light-sensitive element 320). For example, the outputs of a first subset of light-sensitive elements of the imager could be sampled at a high rate by high-frequency ADCs and the outputs of a second subset of light-sensitive elements of the imager could be input into respective analog frontend circuitry as described herein. In another example, analog circuitry could be configured to detect the presence of a speckle event in the output of a light-sensitive element, and a high-frequency ADC could be operated responsively to sample the output of the light-sensitive element for a specified period of time after the detection of the speckle event by the analog circuitry (i.e., the operation of the ADC could be triggered by the detection of the speckle event by the analog circuitry). Other embodiments of analog and/or digital circuitry to determine one or more flow properties in an environment based on the outputs of one or more light-sensitive elements are anticipated.

Note that the detection of flow properties in blood in a portion of subsurface vasculature 307 of an arm 305 based on scattering of coherent illumination by scatterers (e.g., illustrative blood cell 309) in the portion of subsurface vasculature 307 and the detection of flow properties in the blood due to time-dependent changes in the detected time-varying pattern of constructive and destructive interference in the scattered light emitted by the tissue of the arm 305 is intended as a non-limiting illustrative example of the detection of flow properties in environments that scatter light and that include scatterers that have time-dependent properties (e.g., location, orientation) related to flow in the environment. For example, the environment could be any tissue of a human (e.g., an ankle, an ear, a neck, a portion of central vasculature, a tumor, a tissue undergoing a surgical intervention and/or exposed during such an intervention) or animal, and the flow properties could be a property of flow in any fluid of the human or animal body (e.g., arterial blood, capillary blood, venous blood, lymph, interstitial fluid, stomach or other digestive contents, air in the airways and/or lungs, cerebrospinal fluid). The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, a, or some other environment. In another example, the fluid could be a fluid of a microfluidic assay or other microfluidic device or assembly. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., functionalized nanodiamonds and functionalized magnetic particles) to the environment.

In some examples, systems and methods as described herein could be applied to determine flow properties in biological tissues that are subject to a surgical intervention. That is, flow properties could be determined in a portion of biological tissue that has been exposed during a surgical intervention, that contains a target to be ablated, excised, resected, or otherwise manipulated (e.g., that contains a tumor, cyst, epileptic center, or infectious agent), that contains a biological structure to be modified (e.g., an aneurysm to be repaired, a vascular anastomosis to be cauterized, a re-entrant conductive cardiac fiber to be severed), that contains a portion of sensitive tissue (e.g., a portion of eloquent cerebral cortex). In such examples, methods and systems as described herein could be applied to determine flows in such biological tissue in order to, e.g., determine a level of perfusion within and/or across the tissue, to determine the location, pattern, width, depth, or other information about vasculature in such a biological tissue, to detect the location of a tumor or other target structure and/or tissue in the biological tissue, or to determine some other information about the biological tissue.

Such determined information could be used to ablate a target (e.g., a tumor whose location has been determined), to avoid damaging a sensitive tissue (e.g., to avoid mechanical or thermal damage to a tissue, to avoid disrupting perfusion of and/or vascular supply to the tissue), to determine a portion a vasculature through which to introduce a drug or other substance, to determine a portion a vasculature from which to extract a blood or other tissue sample, or to accomplish and/or instruct some other application(s). Such determined information could be presented to a human surgeon (e.g., via a heads-up-display, via a control console of a robotic surgical system) to inform the performance of a surgical intervention by the surgeon and/or used to determine the operation of a robotic surgical system (e.g., to automatically or semi-automatically ablate a target tissue at a determined location while avoiding damaging sensitive tissues by, e.g., avoiding inflicting damage to vasculature perfusing such sensitive tissue).

Scatterers in the environment could be discrete particles (e.g., blood cells, other cells, micelles, vacuoles, immiscible globules (e.g., oil globules in water), engineered particles (e.g., quantum dots, PEG particles, microparticles of a conductive, semiconductive, magnetic, or other material)) in the environment, or could be discontinuities within the fluid whose flow is being determined (e.g., cavitation bubbles, localized turbulence, high thermal and/or pressure gradients, shock waves). The scatterers could be present in the environment (e.g., cells in blood or other biological fluids, microorganisms, particles of silt, or other scatterers in an environmental fluid (e.g., a stream, a pond)) or could be introduced (e.g., production of cavitation bubbles by application of directed energy and/or mechanical intervention, injection of scattering particles (e.g., functionalized particles) into the bloodstream of a human or animal).

Scatterers in an environment could have one or more properties that can be detected and that are related to one or more properties of the environment. For example, a scatterer could selectively interact with an analyte of interest (e.g., the scatterer could be functionalized with a bioreceptor specific to the analyte) and a drag coefficient or other property of the scatterer could be related to the scatterer binding to the analyte. Thus, detection of the velocity of such an individual scatterer or population of such scatterers, relative to one or more determined and/or detected flow properties of the environment containing the scatterer(s), could enable determination of one or more properties of the analyte (e.g., a concentration of the analyte).

Those of skill in the art will understand the term "scatterer" in its broadest sense and that it may take the form of any natural or fabricated material, a cell, a protein or aggregate of proteins, a molecule, cryptophan, a virus, a micelle, a phage, a nanodiamond, a nanorod, a quantum dot, a single-magnetic-domain crystal of a metal, etc. that can interact with light incident on the scatterer to reflect, refract, diffract, or otherwise scatter the incident light. Scatterers could be naturally present in an environment of interest (e.g., blood cells in a portion of subsurface vasculature) or could be added to the environment of interest. Further, a scatterer may be of any shape, for example, spheres, rods, non-symmetrical shapes, etc., and may be made of a solid, liquid or gaseous material or combinations thereof.

III. EXAMPLE DEVICES

Figure 4:
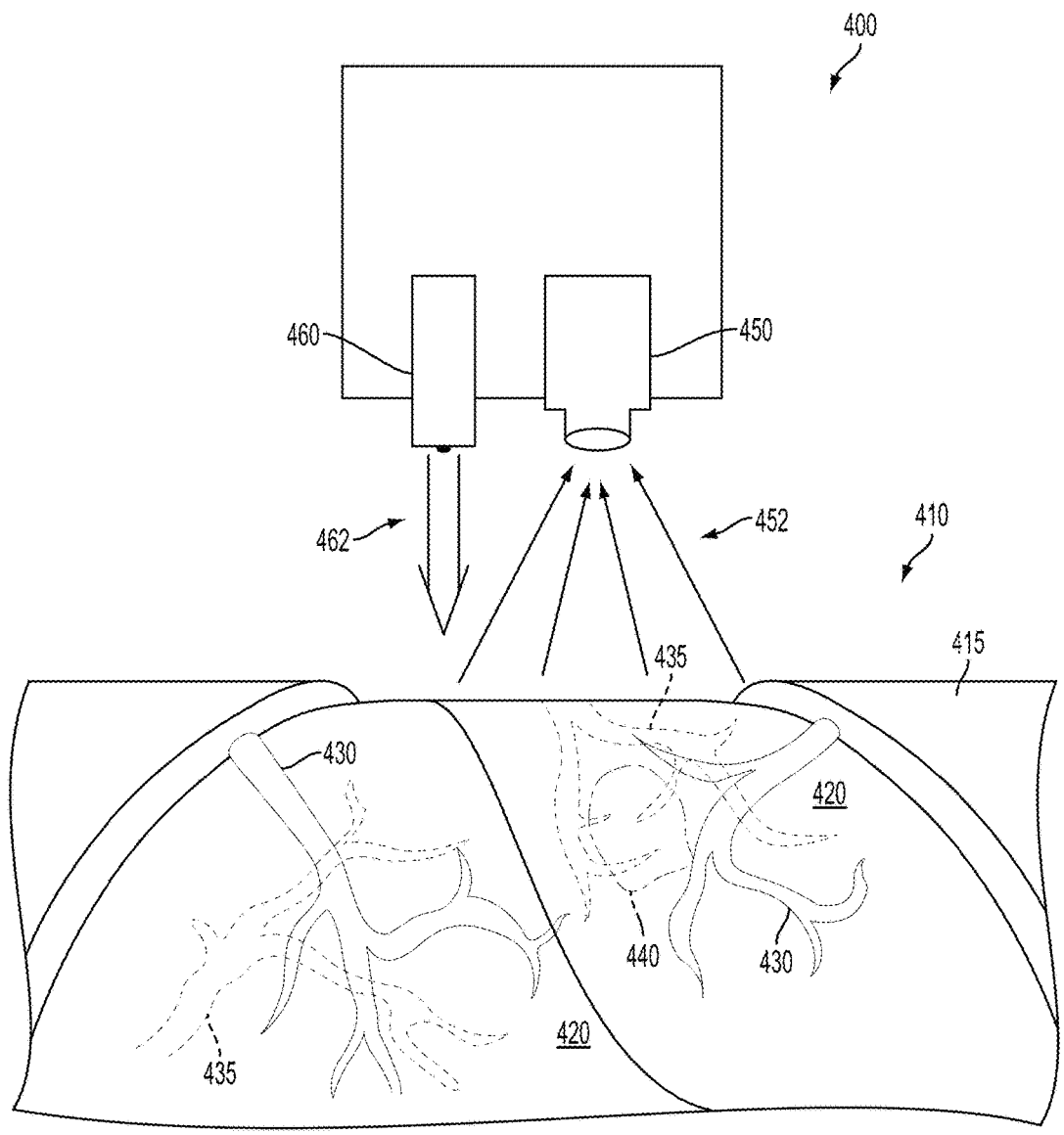
FIG. 4 is a perspective view of an example device, while measuring fluid flow in biological tissue.

A device 400 as illustrated in FIG. 4 can determine flow properties (e.g., a flow rate, a velocity of one or more particles in a fluid flow, or some other properties of flow at and/or through one or more locations or regions) in a biological tissue 410 by emitting a beam of coherent illumination 462 into the biological tissue 410 using a laser 460 and detecting time-varying patterns of constructive and destructive interference in emitted light 452 that is emitted from a plurality of portions (e.g., areas) of the biological tissue 410 in response to illumination using an imager 450. The biological tissue 410 can be any environment containing scatterers (e.g., blood cells, other cells, organelles, cell walls, vessel walls) such that the scatterers and other elements of the biological tissue 410 scatter the beam of coherent light 462 in a manner that causes the time-varying patterns of constructive and destructive interference in the emitted light 452 to have one or more properties related to flow properties in the biological tissue 410.

As illustrated in FIG. 4, the biological tissue 410 includes biological tissues undergoing a surgical intervention. The biological tissue 410 includes skin 415 that has been cut and retracted to expose underlying tissues that could be subject to further surgical intervention. The underlying tissues include bulk tissue 420 (e.g., muscle tissue, brain tissue, liver tissue, breast tissue, or some other biological tissue(s)) and a target tissue 440 (e.g., a tumor, neoplasm, cyst, anastomosis, aneurism, epileptic focus, or some other target of a surgical intervention) within the bulk tissue 420. Surface vessels 430 and deep vessels 435 are present on the surface of and within the bulk tissue, respectively. Flow properties in the biological tissue 410 could be detected for surface regions of the biological tissue 410 (e.g., for fluid flows within the surface vessels 430 and/or in interstitial tissue, capillary beds, and/or microvasculature near the surface of the bulk tissue 420) and/or for deeper tissues. Further, the device 400 could be configured to detect flow properties of biological tissues through overlying tissues. In some examples, flow properties in the bulk tissue 420, vessels 435, 435, and/or target tissue 440 could be detected and/or determined by illuminating and detecting light emitted from such tissues through a layer of overlying tissue such that such flow properties could be detected and/or determined without cutting through and/or retracting the skin 415.

The imager 450 and laser 460 could be configured as illustrated in FIG. 4 (i.e., separate, parallel, non-coaxial) or could be configured in another way, according to an application. In some examples, the imager 450 and laser 460 could be coupled to a set of optical elements to enable some function. In an example, the direction of the beam of coherent illumination 462 emitted by the laser 460 could be controllable using some apparatus, for example a set of galvanometer-driven mirrors. The galvanometers could be operated such that flow properties in specified regions (where the beam from the laser is directed) could be illuminated such that flow properties in the specified regions could be determined. Other configurations and applications are anticipated.

The imager 450 is configured to detect time-varying patterns of constructive and destructive interference in light emitted from a plurality of portions of the biological tissue 410 in response to illumination from the laser 480. In a non-exhaustive list, the imager 450 may include one or more photodiodes, phototransistors, photoresistors, active pixel sensors, CCDs, cameras, angle-sensitive pixels, or some other light-sensitive elements configured to detect one or more properties of time-varying patterns of constructive and destructive interference in light emitted from respective portions of the biological tissue 410. The components of the device 400 may be miniaturized so that the device 400 may be used to detect flow properties in the biological tissue 410 while minimally impeding access to the biological tissue 410, e.g., to cut, ablate, resect, retract, palpate, cauterize, suture, clamp, or otherwise manipulate or interact with the biological tissue 410.

The laser 460 and/or imager 450 could include one or more lenses, filters, collimators, diffraction gratings, or other elements according to an application. For example, the imager 460 could include a filter such that light-sensitive elements of the imager 450 only receive light at wavelengths corresponding to a wavelength of light 462 emitted by the laser 460. In another example, the laser 460 could include a polarizing filter or could be otherwise configured such that the emitted beam of coherent illumination 462 is polarized in a first specified direction. The imager 450 could also include a polarizing filter or other optical element(s) such that light-sensitive elements of the imager 450 are prevented from receiving light emitted from the biological tissue 410 that is polarized in the first specified direction (e.g., the imager 450 could include a polarizing filter that is oriented perpendicularly to the first specified direction). When the device 400 is configured in such a manner, light-sensitive elements of the imager 450 could be substantially prevented from receiving light from the laser 460 that is directly reflected from the surface of the biological tissue 410 (e.g., light from specular reflections). This could increase a signal-to-noise ratio of signals generated by light-sensitive elements of the imager 450 by increasing the contribution of scattered light to the signals relative to the contribution of specular reflection light that is not related to flow properties in the biological tissue 410.

The device 400 could be configured to emit beams of coherent illumination 462 at two or more different wavelengths during two or more different periods of time. This could include the laser 460 being a tunable laser such that one or more properties (e.g., a cavity length, a gain medium refractive index, a reflectivity spectrum of a mirror) of the laser 460 are controllable to control the wavelength of coherent illumination emitted by the laser. Additionally or alternatively, emitted beams of coherent illumination 462 having different wavelengths could include the device 400 having two more different lasers configured to emit coherent illumination at two or more respective different wavelengths. Such a device 400 could be operated to emit beams of coherent illumination 462 at different wavelengths according to a variety of applications. In some examples, emitting coherent beams of illumination 462 at different wavelengths into the biological tissue 410 could allow for the detection of respective different flow properties in the biological tissue 410. For example, first and second wavelengths could be selectively scattered by first and second sets of scatterers in the biological tissue 410, respectively, allowing for the detection of flow properties in the biological tissue 410 corresponding respectively to movements of the first and second sets of scatterers. In another example, the first and second wavelengths could have different penetration depths, degrees of scattering in the biological tissue 410, degrees of scattering in particular regions (e.g., types of tissue) in the biological tissue 410, or some other differential interaction with elements and/or regions of the biological tissue 410 such that emission of beams of coherent illumination at two or more different wavelengths could allow for detection of flow properties in different regions (e.g., at different depths, in different types of tissue) of the biological tissue 410.

Further, emitting beams of coherent illumination 462 at two or more different wavelengths during two or more different periods of time could allow for determination of spectrographic properties of the biological tissue 410. For example, a reflectivity, absorption, scattering, excitation, emission, or other type of spectrum or spectrographic information could be determined for regions of the biological tissue 410. Such determined spectrographic information could be used to determine flow properties in the biological tissue 410 or to determine some other information about the biological tissue 410. For example, the device 400 could emit first and second beams of coherent illumination (e.g., from respective first and second lasers of the device 400) at respective different first and second wavelengths (e.g., at a red wavelength and a near-infrared wavelength). A level of blood cell oxygenation in one or more particular regions of the biological tissue 410 could be determined based on properties (e.g., intensities) of light emitted from the one or more particular regions of the biological tissue 410 in response to illumination by the first and second beams of illumination (e.g., based on knowledge of absorption spectra of oxygenated and of deoxygenated hemoglobin in blood cells). Other applications of spectrographic information about the biological tissue 410 detected using the device 400 are anticipated.

The device 400 may additionally include additional detectors or other systems for detecting other physiological parameters of the biological tissue 410, which could include any parameters that may relate to the health of the person whose body includes the biological tissue 410. For example, the system 400 could include detectors configured to pulse rate, respiration rate, temperature, the presence of fluorophores or other markers in the biological tissue 410, the presence of an analyte in the tissue, a water content of portions of the tissue, a hydrogen content of portions of the tissue, an internal geometry and/or anatomy of the tissue, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor. Additionally or alternatively, the laser 460 and/or imager 450 could be configured and/or operated to allow the detected of the other physiological parameters. For example, a pulse rate could be detected by determining and/or detected a flow property within the biological tissue over time (e.g., to detect a frequency of pulses of the determined flow within an artery in the biological tissue). In another example, the laser 460 could be used to excite a fluorophore and/or the imager 450 could be used to detect light emitted by a fluorophore in the biological tissue 410 to allow the detection of the fluorophore in the biological tissue 410.

The laser 460 is configured to transmit a beam of coherent illumination 462 that can penetrate the biological tissue 410, for example, into a lumen of vessels on the surface 430 and/or within 435 the bulk tissue 420. The transmitted illumination can be any kind of illumination that is benign to the biological tissues 420 and that results at least in scattering of the beam of illumination to produce time-varying patterns of constructive and destructive interference in light emitted from the biological tissue that are related to the disposition of scatterers (e.g., blood cells) in fluid flows (e.g., blood flows, interstitial fluid flows) in the biological tissue 410. The wavelength of the transmitted illumination could be specified to penetrate biological tissues; for example, the transmitted illumination could have a wavelength within a near-infrared (NIR) transparency window of biological tissue (e.g., between approximately 780 nanometers and approximately 810 nanometers). The wavelength of the transmitted illumination could be specified to be a wavelength that is scattered by blood cells. The wavelength of the transmitted illumination could be between approximately 400 nanometers and approximately 1000 nanometers.

The device 400 could be secured relative to the biological tissue 410 and/or some other tissues and/or surgical instrument(s) in a variety of ways. The components of the device 400 may be disposed on or within a mount or housing or on some other structure for mounting the device 400 to enable stable detection of flow properties in the biological tissue 410 or other functions relative to elements in a surgical environment, for example, to a surgical frame secured relative to the biological tissue 410 located within a body cavity that is subject to a surgical intervention. The surgical system 400 could include additional components. Device 400 may take a variety of forms, such as a wall, surgical table, ceiling, or floor-mounted device. Device 400 could also take the form of a system, device, or combination of devices that is configured to be part of another device, apparatus, or system. For example, device 400 could take the form of an imager, laser, and/or other components configured to be mounted to or otherwise disposed as part of a surgical apparatus, tool, implement, or system (e.g., a robotic surgical system, a stereotactic surgical apparatus, a laparoscopic and/or endoscopic surgical system). Device 400 could also take the form of a system configured to detect flow properties in some other industrial environment, medical environment, scientific environment, or some other environment. Surgical Device 400 could also take other forms Flow properties or other information detected and/or determined by the device 400 could be used to inform the performance of wholly or partially automated surgical interventions on the biological tissue 410. In some examples, this could include determining, based on detected and/or determined flow properties in the biological tissue 410, regions of the biological tissue 410 to avoid interaction with. For example, a portion of the biological tissue 410 could be determined to contain a blood vessel (e.g., 430, 435), a nerve, a tendon, a portion of eloquent cortex, or some other sensitive tissue(s), and this determination could be used by an automated surgical system to avoid ablating, heating, cutting, abrading, debriding, cauterizing, contusing, stretching, or otherwise directing energy toward or interacting with the portion of the biological tissue 410. In some examples, such information about the portions of the biological tissue 410 could be used to determine the efficacy and/or effects of an automated or other surgical intervention, e.g., to determine whether a cancerous tissue has been fully ablated by the operation of a surgical laser or other surgical instrument, to determine whether perfusion of a particular tissue has been temporarily or permanently altered, or to determine some other property of the biological tissue 410.

The device 400 may also include and/or be in communication with a user interface (e.g., a display, not shown) via which a user of the device 400 (e.g., a surgeon) may receive information about the determined flow properties in the biological tissue 410 and/or other information about the biological tissue 410 (e.g., the location, pattern, depth, and/or extent of vasculature in the biological tissue 410, a degree of perfusion within different portions of the tissue 410, the location and extent of a target tissue, e.g., tumor, within the biological tissue 410). Such information could be provided on a wall-mounted display, a handheld display, a heads-up display worn by a surgeon, or some other display means. In some examples, such information could be provided through a console of a tele-surgical system. The device 400 (e.g., a laser and imager configured as described herein to detect flow properties in a biological tissue) could be incorporated as part of a robotic surgical system controlled by such a console, e.g., could be disposed on a robotically-actuated arm to control the location of the elements of the device 400 relative to one or more biological tissues that are subject to a surgical intervention.

A device as described herein (e.g., 400) could be configured to determine and/or detect flow properties in a biological tissue (e.g., 410) as illustrated herein, or could be configured and/or operated to determine and/or detect flow properties in some other environment of interest. The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, or some other environment. The environment could be one or more portions of a microfluidic assay, process, or other microfluidic assembly. The environment could include a liquid, a gel, or some other phase of matter or combination of phases (e.g., an emulsion). The environment could include biological samples that had been freeze-dried, desiccated, frozen, vaporized, alkalated, or otherwise prepared, including adding natural and/or artificial scatterers to the environment.

IV. EXAMPLE DETERMINATION OF FLOW PROPERTIES IN BIOLOGICAL TISSUE

Systems and methods described herein relate to the detection and/or determination of flow properties in biological tissues and other environments containing scattering elements by illuminating the biological tissue with coherent illumination and detecting patterns of constructive and destructive interference in light responsively emitted from a plurality of portions of the biological tissue in response to the illumination. A variety of flow properties (e.g., flow rates, flow directions, velocity distributions of scattering elements in fluid flows) could be detected at a plurality of points on and/or within the biological tissue. For example, the plurality of flow properties could include a plurality of flow rates of blood cells in the biological tissue (e.g., in blood within arteries, veins, or other vasculature in the tissue, in interstitial fluid of the tissue, in some other fluid flow in the tissue). Further, detection of time-varying patterns of constructive and destructive interference in light could include detecting a variety of properties of the emitted light (e.g., intensity, amplitude, polarization, frequency content, patterns of change over time of various properties) at one or more points in time using a variety of methods.

Determining a plurality of flow properties in biological tissue (or some other environment of interest) could include determining one or more flow properties (e.g., a mean flow rate, a distribution of velocities of scatterers in a fluid flow) in a plurality of volumes, areas, or other regions of the biological tissue. For example, flow properties could be determined for a plurality of regions across an area of biological tissue, e.g., at a plurality of points having a regular spacing across the biological tissue. Such points could correspond to a plurality of portions of the biological tissue from which respective light-sensitive elements of an imager receive light. Additionally or alternatively, flow properties could be determined for a plurality of regions within a volume of biological tissue, e.g., at a plurality of points having a regular or otherwise specified spacing within a specified distance from a surface of the biological tissue. Further, a resolution (i.e., a spacing between such points for which flow properties are determined) of such a determination could be related to the depth beneath a surface of the biological tissue. For example, a resolution at which flow properties can be determined in a biological tissue could reduce with increasing depth beneath a surface of the biological tissue due, e.g., to scattering of coherent illumination by elements in additional intervening portions of the biological tissue between a source of illumination and/or imager and such deeper tissues.

Figure 5A:
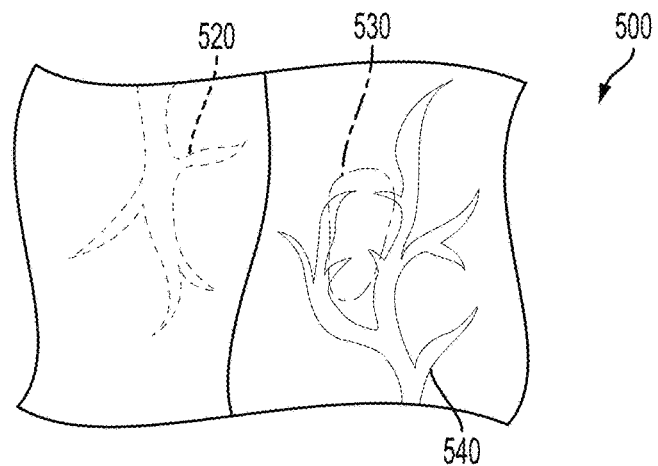
FIG. 5A is a top view of a biological tissue.

Determining flow properties for such a regular or otherwise spaced set of points in a biological tissue could allow for the determination of a map vasculature or other structures within the biological tissue. For example, the extent of different types of tissue and/or volumes within the biological tissue based on information about flow properties of such types of tissue or volumes. As an illustrative example, FIG. 5A shows a biological tissue 500 (e.g., muscle tissue, brain tissue, liver tissue, breast tissue, or some other biological tissue(s)) containing a target tissue 530 (e.g., a tumor, neoplasm, cyst, anastomosis, aneurism, epileptic focus, or some other target of a surgical intervention). The biological tissue 500 additionally includes surface vessels 540 and deep vessels 520 on the surface of and within the biological tissue 500, respectively. The target tissue 530 exhibits increased blood cell flow (e.g., due to having more 'leaky' capillaries than surrounding tissues) or some other flow properties that are different from surrounding non-target tissues. Further, the surface vessels 540 perfuse the target tissue 530 (i.e., provide more branches of vasculature and/or a greater fluid flux to) more than surrounding non-target tissues.

Figure 5B:
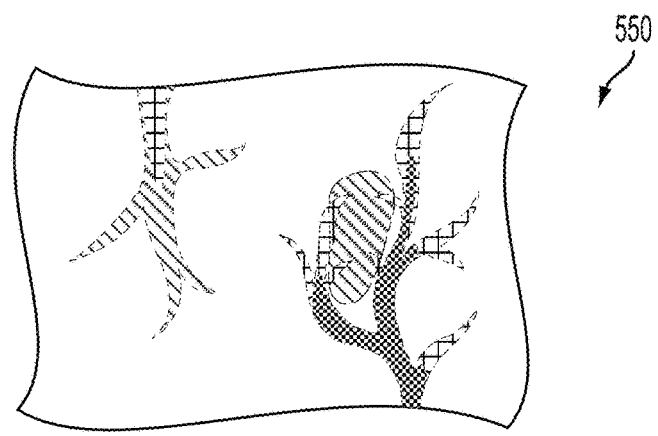
FIG. 5B is a flow map of the biological tissue of FIG. 5A.

Flow properties in the biological tissue 500 could be detected for a plurality of points and/or portions on the surface of and/or within the biological tissue 500 using systems and/or methods described herein. Such determined flow properties could be used to generate a map of flow properties (e.g., flow rates of blood or other fluid) within and/or across the biological tissue 500. FIG. 5B illustrates an example flow map 550 corresponding to the biological tissue 500 illustrated in FIG. 5A. As illustrated, white regions indicate regions of low flow, while darker and/or more hatched regions indicate regions of greater flow. Thus, the target tissue 530 corresponds to a region of the flow map having a higher flow rate than surrounding regions of the biological tissue 500 but slower than regions of blood flow within the blood vessels 520, 540. Further, the flow map shows that the blood vessels 520, 540 exhibit greater flow rates in central regions (e.g., trunks of the vessels 520, 540) than in branches. Further, the deep vessels 520 exhibit lower flow rates than the surface vessels 540.

Other flow properties and/or information determined therefrom could be used to generate maps of the biological issue 500. For example, the depth of blood vessels, depth of regions of greater flow, flow rate pulsatility, blood cell oxygenation, or some other information could be mapped across and/or within the biological tissue 500. Further, such maps or other information about flow properties within and/or across the biological tissue 500 could be used to determine the location, pattern, extent, depth beneath a surface of the biological tissue 500, or other properties of tissues, structures, or other elements within the biological tissue 500.

Figure 5C:
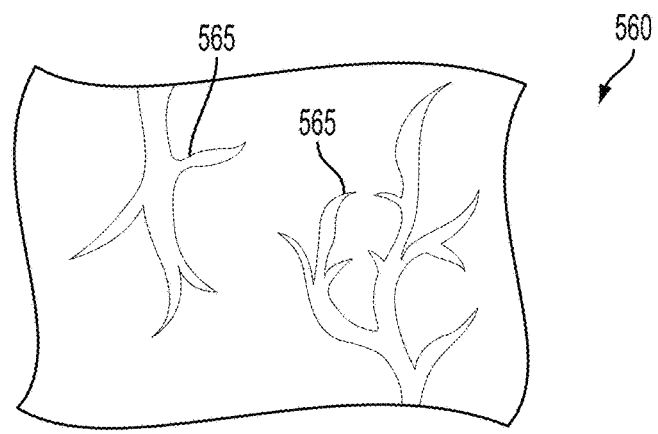
FIG. 5C is a map of vasculature of the biological tissue of FIG. 5A.

For example, a map of vasculature within the biological tissue 500 could be determined based on a determined plurality of flow properties in the biological tissue 500. As an example, FIG. 5C illustrates an example vasculature map 560 corresponding to the biological tissue 500 illustrated in FIG. 5A. The vasculature map 560 indicates vessel extents 565 determined based on a plurality of determined flow properties in the biological tissue 500 (e.g., flow properties represented by the flow map 550). Alternatively or additionally, such a vasculature map could describe the trajectories within the volume of a biological tissue 500, depths, widths, patterns of connection, flow rates, degrees of fluid flux, distributions of velocity of contained blood cells, or other information about portions of vasculature in a biological tissue. Such maps could be two-dimensional (e.g., indicating the locations or other information about vasculature within a biological tissue relative to a two-dimensional surface, e.g., a surface of the biological tissue) or three-dimensional (reporting the trajectories and other information about the location and extent to vasculature throughout a volume of biological tissue).

Such determined maps or other information describing the location of vasculature in a biological tissue could be used in a variety of applications. A determined map of vasculature could be used to avoid damaging vasculature of a tissue when performing a surgical intervention in the tissue. For example, a surgeon and/or robotic surgical system could avoid ablating vasculature of a biological tissue when operating to ablate a target tissue (e.g., a tumor). Additionally or alternatively, a surgical plan could be determined based on a map of the vasculature to avoid disrupting or reducing perfusion to a particular region of tissue, e.g., a nerve, a portion of eloquent cortex, a functional portion of cardiac muscle.

Such a map of vasculature, and determined flow properties of surrounding tissue determined during a surgical intervention, could additionally be used to determine a degree of ischemia applied to biological tissues due to the surgical intervention (e.g., due to ablating, cauterizing, or otherwise damaging blood vessels). Further, such information could be determined to assess the outcome of a surgical intervention, e.g., to determine that a blood vessel has been successfully cauterized, that a blockage has been successfully removed from a blood vessel, or the degree of success of some other surgical intervention. Additionally or alternatively, such information could be used to detect that there is additional blood flow than expected and/or that there is a hemorrhage is a biological tissue (e.g., due to a surgical intervention) and to surgically address such conditions (e.g., to cauterize, ligate, compress, or otherwise stop such flows of blood). Such determinations could be used to estimate a surgical outcome and/or to determine a plan of post-surgical treatment and/or therapy.

Additionally or alternatively, determined map of vasculature could be used to determine particular regions of a biological tissue (e.g., particular portions of vasculature) to interact with during a surgical intervention. For example, a determined map of vasculature could be used to determine the location of a tumor or other target tissue by locating, in the map, regions exhibiting increased vascularization (e.g., regions proximate to the target tissue 530 illustrated in FIG. 5A), vascularization exhibiting a pattern (e.g., a pattern of parallel vasculature indicating a particular type of tissue, e.g., muscle), or determining the location of a target by some other method. In another example, the location of a particular portion of vasculature to inject a substance into (e.g., a drug) and/or to extract blood from (e.g., to perform some analysis) could be determined based on a map of the vasculature. Additionally or alternatively, a location of a portion of vasculature to cauterize (e.g., to destroy an arteriovenous anastomosis, to enable repair or removal of an aneurism, to reduce perfusion to a downstream region of tissue, e.g., a tumor) could be determined based on a map of the vasculature. Other applications of maps of vasculature in a biological tissue are anticipated.

Such a determined map of vasculature within or other determined information about biological tissue could be presented and/or indicated (e.g., to a surgeon) in a variety of ways. For example, a display could be operated to indicate such a determined vasculature map, or to indicate some other information or map related to flow properties or other information about a biological tissue. Such a display could be a standalone display (e.g., a screen present in a surgical environment), a display on a hand-held device configured as described herein to detect and/or determine flow properties in a biological tissue, a display of a heads-up display (e.g., worn by a surgeon), a display of a console of a tele-surgical system, or some other means of display or indication. Such displays could be operated to indicate additional information; for example, a map of vasculature (or some other information) of a biological tissue could be overlaid on an optical image (e.g., generated using a color or black-and-white camera) of the biological tissue. The location, extent, depth, or other information about a target tissue (e.g., a tumor, a portion of vasculature to cauterize, a portion of vasculature into which to inject a substance and/or from which to extract a sample) could additionally or alternatively be determined and indicated. Other methods and/or means of indicating determined information as described herein are anticipated.

Flow properties in a biological environment could be determined based on detected time-varying patterns of constructive and destructive patterns in light emitted from the biological environment in a variety of ways. In some examples, flow properties in a particular portion of tissue (and/or neighboring regions of tissue) could be determined from information (e.g., an intensity waveform, a frequency spectrum and/or content thereof) contained in the time-varying pattern of constructive and destructive interference in light received from the particular portion of tissue. Additionally or alternatively, flow properties in a particular portion of tissue could be determined based on information about time-varying patterns of constructive and destructive interference in light received from a plurality of portions of the biological tissue during one or more time periods and/or points in time.

For example, flow in a portion of biological tissue could be determined by determining a contrast between one or more properties of patterns of constructive and destructive interference in light received from a number of different proximate portions of biological tissue. This could include generating an image of the biological tissue by detecting an average intensity of the time-varying patterns of light received from a plurality of portions of the biological tissue over a specified period of time (e.g., an exposure duration). Contrast in such an image could be determined by a variety of methods (e.g., Weber contrast, Michelson contrast, RMS contrast) and used to determine a relative amount of flow in a portion of the biological tissue based on a determined amount of contrast in the image that corresponds to the portion of the biological tissue. One or more properties of the specified period of time (e.g., the exposure duration of the period of time) could be specified relative to an application (e.g., to set a level of flow detected using this method, a resolution of flow levels detected using this method). Additionally or alternatively, a detected intensity, speckle rate, polarization, or other detected property of light received from a portion of biological tissue could be compared to detected properties of light received from surrounding portions to form a baseline or to allow some other determination, e.g., to determine a noise floor, to set a threshold, to normalize or otherwise scale detected properties, or according to some other application.

Further, such contrast or other spatial computations could be determined at a variety of spatial and temporal resolutions. For example, one or more properties (e.g., an average intensity of received light during a specified time period, a speckle event rate) of light received from each of a plurality of portions of the biological tissue could be averaged, smoothed, or otherwise resampled at a variety of different spatial resolutions, and statistical distributions of the one or more properties across the portions of the biological tissue at the variety of different resolutions could be determined and used to determine flow properties in the biological tissue. Further, such contrast or other spatial determinations could be determined based on detected properties of received light detected at a plurality of different exposures (or based on detected properties of received light applied to different filters, different filter settings, or across a change in some other analog or digital method of processing the detected properties) and flow properties in the biological environment could be determined based on such different determined contrast or other spatial determinations.

Additionally or alternatively, flow properties in a particular portion of biological tissue (and/or neighboring regions of biological tissue, due to multiple scattering of light by scattering elements within the particular portion and neighboring portions) could be determined by detecting and/or determining one or more time-dependent features or properties of a time-varying pattern of constructive and destructive interference in light received from the particular portion of biological tissue. For example, one or more properties of speckle events or other temporal features of a detected waveform of light received from the particular portion of biological tissue could be determined and used to determined flow properties in the particular portion of biological tissue and/or surrounding portions of tissue. Further, detected properties (e.g., intensities) of received patterns of constructive and destructive interference in light could be filtered, time-averaged, or otherwise temporally re-sampled at a variety of different sample rates or resolutions in time (e.g., by setting an exposure time, by averaging a varying number of sampled values of the detected property over time) and statistical distributions of the one or more properties from portion of the biological tissue at the variety of different sample rates or resolutions in time could be determined and used to determine flow properties in the biological tissue.

Additionally or alternatively, frequency content (e.g., a frequency spectrum, a power within one or more ranges of frequencies) of such a detected time-varying pattern of constructive and destructive interference in received light could be used to determine flow properties in a portion of biological tissue. Such determined properties could be used to determine a mean flow rate, a distribution of flow rates, a distribution of scatterer (e.g., blood cell) velocities within a flow, flow properties of multiple fluid flows within a single portion of tissue, or some other information about flow properties in the particular portion of biological tissue.

Figure 6A:
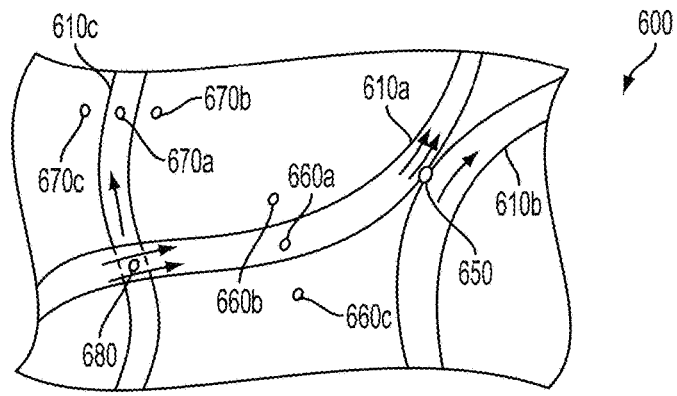
FIG. 6A is a top view of a biological tissue.

FIG. 6A illustrates an example biological tissue 600 including first 610a and second 610b surface vessels and a deeper third vessel 610c location on a surface of and within the biological tissue 600, respectively. A flow rate of blood within the first vessel 610a is greater than flow rates of blood in the second 610b and third vessels 610c (illustrated by the double-arrows within the first vessel 610a and the single arrows within the second 610b and third 610c vessels). The biological tissue 600 could be illuminated by a beam of coherent illumination and time-varying patterns of constructive and destructive interference could be detected in light received from portions of the biological tissue 600 to determine flow properties in the biological tissue 600 (e.g., flow rates of blood and/or blood cells within the blood vessels 610a, 610b, 610c and at other locations within the biological tissue 600) as described herein.

A frequency content (e.g., a frequency spectrum, a power within one or more ranges of frequencies) of detected time-varying patterns of constructive and destructive interference in light received from the biological tissue 600 (e.g., in an intensity of received light detected at a plurality of points in time) could be determined and used to determine flow properties (e.g., flow rates of blood or other fluids, velocity distributions of blood cells or other scatterers in such fluid flows) in portions of the biological environment. Such frequency content could include vector of powers or other values describing the intensity, phase, or other information about the detected light within one or more ranges of frequencies. For example, frequency content could include a power of the detected light within a plurality of ranges of frequencies that are specified at, e.g., linearly, logarithmically, or otherwise regularly-spaced frequencies. Additionally or alternatively, frequency content could include information describing an amplitude, power, width, center frequency, shape, or other properties of one or more peaks or other features of a frequency spectrum of the received light.

Such frequency content could be determined in a variety of ways. For example, an intensity or other property of a time-varying pattern of constructive and destructive interference in light received from a portion of the biological tissue 600 could be sampled at a high rate, and the frequency content could be determined from samples of the intensity using the Fast Fourier Transform, a digital filter, or some other method. Additionally or alternatively, the frequency content could be determined by applying a detected intensity or other property of the received light to one or more filters (e.g., bandpass filters) and determining a power, amplitude, or other output(s) of the filters related to properties of the frequency content.

Determined frequency content could be used in a variety of ways to determine flow properties in or other information about (e.g., depths of blood vessels within) the biological tissue 600. One or more frequency components (e.g., a power within a particular range of frequencies, an amplitude, center frequency, shape, width, or other property of a peak or other feature of frequency content) of such determined frequency content could be determined and used to determine information about the biological tissue 600. For example, a center frequency of a peak in the frequency content of light received from a particular portion of biological tissue could be used to determine a flow rate of fluid within and/or near the particular portion of biological tissue. Further, properties (e.g., center frequencies) of multiple peaks in the frequency content could be used to determine flow rates of multiple fluid flows within and/or near the particular portion of biological tissue (e.g., within multiple blood vessels within and/or near the particular portion of biological tissue).

Figure 6B:
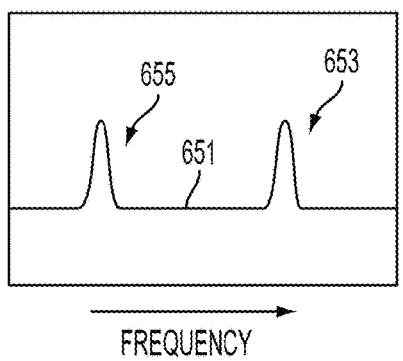
FIG. 6B illustrates frequency content of a signal detected from the biological tissue of FIG. 6A.

FIG. 6B illustrates first example frequency content 651 (e.g., a frequency spectrum) of a time-varying pattern of constructive and destructive interference in light received from a first particular portion 650 of the biological tissue 600. The first particular portion 650 is proximate to the first 610a and second 610b blood vessels, such that light received from the first particular portion of tissue 650 includes light scattered by scatterers (e.g., blood cells) in fluid flows (e.g., blood flows) within both the first 610a and second 610b blood vessels. The horizontal axis indicates frequency (increasing to the right) and the vertical axis indicates power. The first example frequency content 651 illustrates the power at various frequencies of the received light. The first example frequency content 651 includes a first peak 653 having a center frequency greater than the center frequency of a second peak 655. The first 653 and second 655 peaks could correspond to illumination received from the first particular portion of tissue 650 that is scattered, refracted, diffracted, reflected, or that otherwise interacts with scattering elements (e.g., blood cells) flowing in the first 610a and second 610b vessels, respectively. An absolute or relative rate (e.g., a mean velocity) of blood flow within the first 610a and second 610b vessels could be determined based on absolute or relative center frequencies of the first 653 and second 655 peaks, respectively. Further, additional information (e.g., a distribution and/or variance of the velocity of blood cells in the first 610a and second 610b blood vessels) could be determined based on additional properties of the peaks 653, 655 (e.g., a width, shape, or other feature or property of the peaks 653, 655).

Figure 6C:
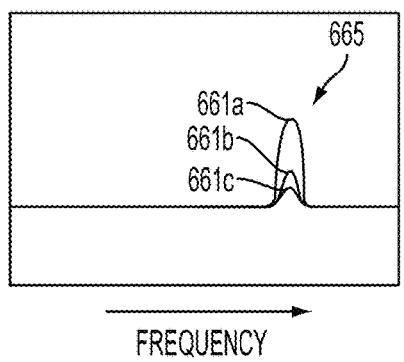
FIG. 6C illustrates frequency content of signals detected from the biological tissue of FIG. 6A.

Due to multiple scattering of light within the biological tissue 600 and/or other interactions between illumination and the biological tissue 600, movement of scatterers (e.g., movement of blood cells) in fluid flows (e.g., blood flows in blood vessels) in the biological environment could have effects on time-varying patterns of constructive and destructive interference in light emitted from portions of the biological tissue 600 across a region proximate to the moving scatterers. Due to scattering, absorption, or other mechanisms, such an effect could be reduced with increasing distance from the moving scatterers. FIG. 6C illustrates second 661a, third 661b, and fourth 661c example frequency contents (e.g., frequency spectra) of time-varying patterns of constructive and destructive interference in light received from second 660a, third 660b, and fourth 660c particular portions of the biological tissue 600, respectively. The second particular portion 660a is more proximate to the first blood vessel 610a than are the third 660b and fourth 660c particular portions. The horizontal axis indicates frequency (increasing to the right) and the vertical axis indicates power. The example frequency contents 661a, 661b, 661c illustrate the power at various frequencies of the received light.

The example frequency contents 661a, 661b, 661c include respective peaks 665 that could correspond to illumination received from the second 660a, third 660b, and fourth 660c particular portions of tissue that is scattered, refracted, diffracted, reflected, or that otherwise interacts with scattering elements (e.g., blood cells) flowing in the first vessel 610a. Due to scattering and/or absorption of light within the biological tissue 600, relative amplitudes of the peak 665 in the third 661b and fourth frequency contents are less than the amplitude of the peak 665 in the second frequency content. Information about the biological tissue 600 and/or about the particular portions of the biological tissue 660a, 660b, 660c (e.g., a scattering spectrum and/or absorption spectrum, a relative and/or absolute degree of scattering and/or absorption, a mean length between scattering events, a width of the first vessel 610a, a depth of the first vessel 610a beneath a surface of the biological tissue 600) could be determined based on such determined frequency contents (e.g., 661a, 661b, 661c) from portions of the biological tissue 600. For example, a degree, shape, pattern, or other property of the decrease in the peak amplitude with distance from the first vessel 610a or from some other location could be determined and used to determine some property of the biological tissue 600.

Figure 6D:
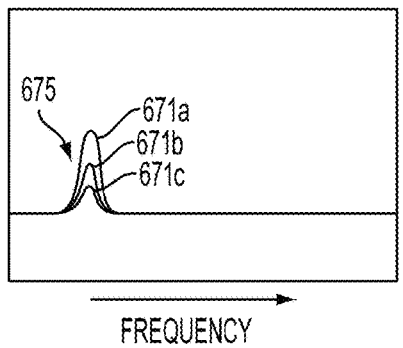
FIG. 6D illustrates frequency content of signals detected from the biological tissue of FIG. 6A.

In some examples, the depth of blood vessels or other structures within the biological tissue 600 could be determined based on a time-varying pattern of constructive interference in light received from one or more portions of the biological tissue 600. For example, an apparent width of a blood vessel, as determined from flow properties determined in portions of biological tissue overlying the blood vessel, could be used to determine a depth of the blood vessel. FIG. 6D illustrates fifth 671a, sixth 671b, and seventh 671c example frequency contents (e.g., frequency spectra) of time-varying patterns of constructive and destructive interference in light received from fifth 670a, sixth 670b, and seventh 670c particular portions of the biological tissue 600, respectively. The fifth particular portion 670a is more proximate to the third blood vessel 610c than are the sixth 670b and seventh 670c particular portions. The horizontal axis indicates frequency (increasing to the right) and the vertical axis indicates power. The example frequency contents 671a, 671b, 671c illustrate the power at various frequencies of the received light.

The example frequency contents 671a, 671b, 671c include respective peaks 675 that could correspond to illumination received from the fifth 670a, sixth 670b, and seventh 670c particular portions of tissue that is scattered, refracted, diffracted, reflected, or that otherwise interacts with scattering elements (e.g., blood cells) flowing in the third vessel 610c. Due to scattering and/or absorption of light within the biological tissue 600, relative amplitudes of the peak 675 in the sixth 671b and seventh 671c frequency contents are less than the amplitude of the peak 675 in the fifth 671a frequency content. Thus, the apparent width of the third vessel 610c, as determined based on flow properties determined from detected time-varying patterns of constructive and destructive interference in light received from a plurality of portions of the biological tissue 600, could be wider than the actual width of the third vessel 610a. The depth of the third vessel 610c could be determined based on such a determined apparent width. For example, the depth of the third vessel 610c could be determined based on a relationship between the apparent width of the third vessel 610c and an expected width of the third vessel 610c (e.g., an expected width of vessels in the biological tissue, an expected width of the third vessel 610a that is updated and/or determined based on some other detected information about the biological tissue 600 and/or the third vessel 610c). Such a relationship could be specified (e.g., based on empirical measurements in another biological tissue, based on simulations of scattering of light in the biological tissue 600). Such a relationship could be determined based on some other measurement of the biological tissue 600, for example, a measurement of scattering, absorption, or other optical properties of the biological tissue, e.g., determined as described in combination with the frequency contents illustrated in FIG. 6C.

Figure 6E:
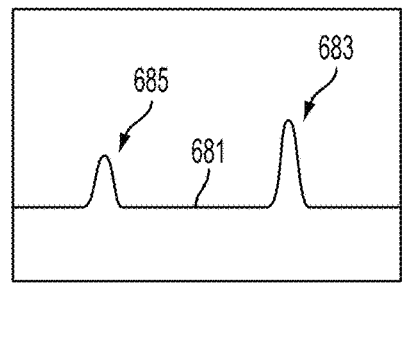
FIG. 6E illustrates frequency content of a signal detected from the biological tissue of FIG. 6A.

In another example, the depth of a vessel beneath a surface of a biological tissue could be determined based on absorption of light emitted and/or scattered by blood cells or other scatterers in the vessel by intervening tissues between the blood vessel and the surface of the biological tissue. FIG. 6E illustrates eighth example frequency content 681 (e.g., a frequency spectrum) of a time-varying pattern of constructive and destructive interference in light received from an eighth particular portion 680 of the biological tissue 600. The eighth particular portion 680 is proximate to the first 610a and third 610c blood vessels, such that light received from the eighth particular portion of tissue 680 includes light scattered by scatterers (e.g., blood cells) in fluid flows (e.g., blood flows) within both the first 610a and third 610c blood vessels. The horizontal axis indicates frequency (increasing to the right) and the vertical axis indicates power. The eighth example frequency content 681 illustrates the power at various frequencies of the received light. The eighth example frequency content 681 includes a first peak 683 having a center frequency and an amplitude greater than the center frequency and amplitude, respectively, of a second peak 685. The first 683 and second 685 peaks could correspond to illumination received from the eighth particular portion of tissue 680 that is scattered, refracted, diffracted, reflected, or that otherwise interacts with scattering elements (e.g., blood cells) flowing in the first 610a and third 610c vessels, respectively.

An absolute or relative rate (e.g., a mean velocity) of blood flow within the first 610a and third 610c vessels could be determined based on absolute or relative center frequencies of the first 683 and second 685 peaks, respectively. Further, an absolute or relative difference in depth of the first 610a and third 610c vessels could be determined based on absolute or relative amplitudes of the first 683 and second 685 peaks, respectively, due, e.g., to attenuation and/or scattering of light from deeper vessels by intervening tissues. Thus, the depth of the third vessel 610c relative to the first vessel 610a and/or the surface of the biological tissue 600 could be determined based on such an absolute or relative difference in frequency components (e.g., peaks) of the determined eighth frequency content 681. For example, the depth of the third vessel 610c could be determined based on a relationship between the amplitudes of the first 683 and second 685 peaks. Such a relationship could be specified (e.g., based on empirical measurements in another biological tissue, based on simulations of scattering of light in the biological tissue 600). Such a relationship could be determined based on some other measurement of the biological tissue 600, for example, a measurement of scattering, absorption, or other optical properties of the biological tissue, e.g., determined as described in combination with the frequency contents illustrated in FIG. 6C. Such a relationship could be further determined based on a determination that a vessel (e.g., 610a) against which the third vessel 610c is to be compared is a surface vessel (as 610a is in the example of FIG. 6A).

The depth (or other information about the location) of a blood vessel in biological tissue could be determined using the methods described above, some other methods, or a combination thereof. For example, the depth of a blood vessel (or other structure in a biological tissue) could be determined based on time-varying patterns of constructive and destructive interference in light emitted from the biological tissues in multiple directions, as detected using multiple imagers. Additionally or alternatively, the biological tissue could be illuminated by multiple beams of coherent illumination, having respective multiple wavelengths, coherence lengths, angles relative to the biological tissue, or other properties.

Further, flow properties in biological tissue could be based on detected time-varying patterns of constructive and destructive interference in light emitted from the biological tissue determined by some other methods. For example, a point spread function or some other relationship could be determined to describe properties of a time-varying pattern of constructive and destructive interference in light emitted from a particular portion of biological tissue based on the contribution of flow properties (e.g., flow rates of scatterers) in the particular portion of biological tissue and in a plurality of nearby portions of tissue. Such a point spread function or other relationship could be based on a distance, angle, or other relationship between the particular portion of tissue and nearby portions of tissue, detected and/or specified properties of the biological tissue, properties of the beam of coherent illumination used to illuminate the biological tissue (e.g., wavelength, coherence length, intensity, angle relative to the biological tissue and/or an imager), properties of an imager used to detect light emitted from the particular portion of tissue (e.g., an angle relative to the biological tissue, an aperture width, a focal length, a resolution), or some other properties of the biological tissue and/or systems configured to interact with the biological tissue to determine flow properties in the biological tissue. Such a point spread function or other relationship could be used to determine flow properties for a plurality of portions of the biological tissue (e.g., for a plurality of regions on the surface of the biological tissue, for a plurality of volumes within the biological tissue) using computed tomography or some other means. Additional methods for determined flow properties in biological tissue based on detected time-varying patterns of constructive and destructive interference in light emitted from the biological tissue in response to illumination by a beam of coherent illumination are anticipated.

V. EXAMPLE ELECTRONICS PLATFORM FOR A DEVICE

Figure 7:
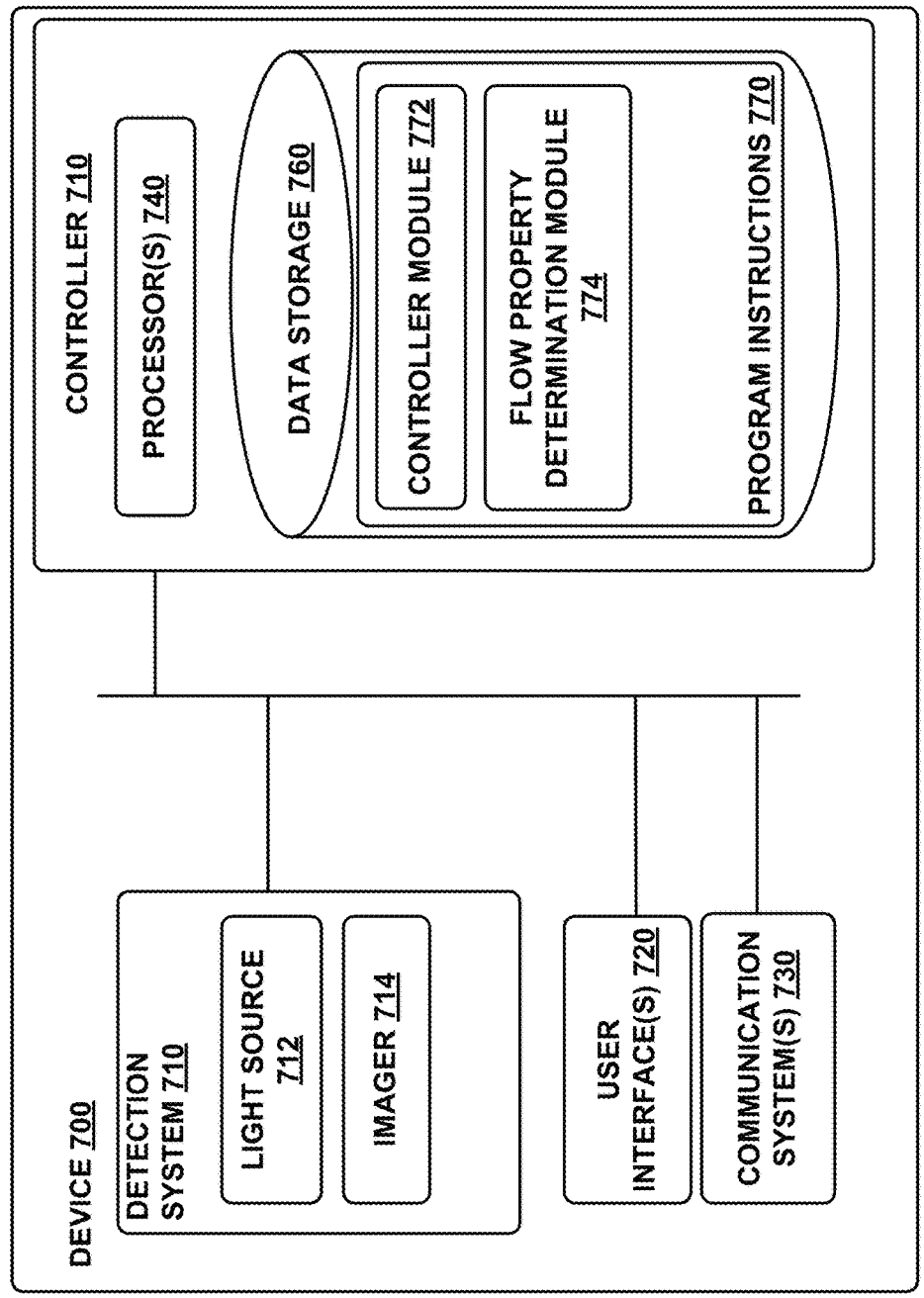
FIG. 7 is a functional block diagram of an example device.

FIG. 7 is a simplified block diagram illustrating the components of a device 700, according to an example embodiment. Device 700 may take the form of or be similar to the device 400 shown in FIG. 4. In some examples, device 700 could take the form of a device configured to be secured relative to biological tissues undergoing a surgical intervention (e.g., tissue of a human body). For example, the device 700 could be configured to be mounted to a surgical frame, a floor, wall, ceiling, or other structure in a surgical environment or operating room, or secured to some other structure. In some examples, the device 700 could be configured to be secured to and/or a part of an endoscope, laparoscope, thoracoscope, or other surgical instrument configured to be inserted into a body cavity. In some examples, the device 700 could be part of a robotic surgical system and/or could be operated to inform the automated or semi-automated operation of such a system. Additionally or alternatively, the device 700 could be part of a robotic surgical system and information generated by the device could be indicated or otherwise presented to a surgeon or other operator of such a robotic surgical system (e.g., indicated on a display of a control console of such a robotic surgical system) to inform the performance of a surgical intervention by the surgeon. However, device 700 may also take other forms, e.g., could take the form of a device configured to be maintained in proximity to some other environment of interest (e.g., a body part, a biological sample container, a volume of a water treatment system) by a user or operator of the device 700 or by a frame or other supporting structure. Device 700 could also take the form of a device configured to illuminate and to detect emitted light from an in vitro biological environment or some other environment, for example, a fluid volume within a water treatment process, a microfluidic environment or assay, or some other environment. Device 700 also could take other forms.

In particular, FIG. 7 shows an example of a device 700 having a detection system 710, a user interface 720, communication system(s) 730 for transmitting data to a remote system, and controller 710. The components of the device 700 may be disposed on a mount or on some other structure for mounting the device to enable stable detection of flow properties in an environment of interest, for example, to a surgical frame such that a portion of biological tissue undergoing a surgical intervention is visible.

Controller 710 may be provided as a computing device that includes one or more processors 740. The one or more processors 740 can be configured to execute computer-readable program instructions 770 that are stored in the computer readable data storage 760 and that are executable to provide the functionality of a device 700 described herein.

The computer readable data storage 760 may include or take the form of one or more non-transitory, computer-readable storage media that can be read or accessed by at least one processor 740. The one or more computer-readable storage media can include volatile and/or non-volatile storage components, such as optical, magnetic, organic or other memory or disc storage, which can be integrated in whole or in part with at least one of the one or more processors 740. In some embodiments, the computer readable data storage 760 can be implemented using a single physical device (e.g., one optical, magnetic, organic or other memory or disc storage unit), while in other embodiments, the computer readable data storage 760 can be implemented using two or more physical devices.

Detection system 710 includes an imager 714 and a light source 712. The light source 712 is configured to emit a beam of coherent illumination (e.g., the light source 712 could include a laser) into an environment of interest (e.g., into a biological tissue). The detection system 710 additionally includes an imager 714 configured to detect a plurality of time-varying patterns of constructive and destructive interference in light emitted from respective portions of the environment of interest in response to illumination from the light source 712 using respective light-sensitive elements of the imager 714. In a non-exhaustive list, the imager 714 may include one or more photodiodes, phototransistors, photoresistors, an active pixel sensor, a CCD, a camera, or some other light-sensitive elements configured to detect one or more properties of time-varying patterns of constructive and destructive interference in light emitted from a plurality of portions of the environment of interest.

The detection system 710 may additionally include additional detectors for detecting other properties of the environment of interest (e.g., for detecting physiological parameters of a human whose body includes the environment of interest). Such additional detected properties could include any parameters that may relate to the health of the person whose biological tissues are being measured by the device 700. For example, the detection system 710 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The detection system 710 could additionally include electronics configured to operate the light source 712 and the imager 714. The electronics could include a high-speed analog-to-digital converter (ADC) configured to sample an output (e.g., a voltage, a current) of one or more light-sensitive elements of the imager 714 at a specified high rate (e.g., one megahertz) to detect features of individual speckle events or other features in the output of the light-sensitive elements of the imager 714 that have one or more properties (e.g., a pulse width, a rise time, a rise rate) related to flow properties in an environment of interest. Additionally or alternatively, the electronics could include analog frontend circuitry that includes analog circuitry configured to filter, decimate, quantize, or otherwise alter and/or perform other analog operations or computations on the output(s) of the imager 714 to produce an output electronic signal that is related to flow properties in the environment (e.g., flow properties in a portion of vasculature). This output electronic signal(s) could then be used (e.g., sampled by an ADC of a microcontroller) to determine the flow properties. The electronics could include a plurality of such analog frontend circuitry configured to receive respective outputs from respective light-sensitive elements of the imager 714 and to output respective electronic signals related to the respective received light-sensitive element output signals. Additionally or alternatively, the electronics could include fewer instances of such analog frontend circuitry, and the outputs of respective light-sensitive elements of the imager 714 could be electronically multiplexed such that the fewer instances of the analog frontend circuitry could be operated in combination with the outputs of the respective light-sensitive elements.

The program instructions 770 stored on the computer readable data storage 760 may include instructions to perform any of the methods described herein. For instance, in the illustrated embodiment, program instructions 770 include a controller module 772 and a flow property determination module 774.

The controller module 772 can include instructions for operating the detection system 710, for example, the light source 712 and the imager 714. For example, the controller module 772 may operate the light source 712 and the imager 714 during each of a set of pre-set measurement periods. In particular, the controller module 772 can include instructions for operating the light source 712 to emit a beam of coherent illumination into a target environment (e.g., tissue of a person) and controlling the imager 714 to detect a plurality of patterns of constructive and destructive interference in light responsively emitted from a plurality of portions the environment being interrogated by the device 400.

The controller module 772 can also include instructions for operating a user interface 720. For example, controller module 772 may include instructions for displaying data collected by the detection system 710 and analyzed by the flow property determination module 774. Further, controller module 772 may include instructions to execute certain functions based on inputs accepted by the user interface 720, such as inputs accepted by one or more buttons or touchscreen displays disposed on the user interface.

Flow property determination module 774 may include instructions for receiving data from and/or operating the data collection system 710, analyzing the data to determine flow properties in the environment (e.g., a flow rate of blood in a portion of vasculature), analyzing the determined flow properties to determine a map of vasculature and/or the location and extent of a target tissue, if a medical condition is indicated (e.g., a hemorrhage, a cessation of perfusion to a sensitive tissue), or other analytical processes relating to the environment proximate to the device 700. In particular, the flow property determination module 774 may include instructions for determining flow properties (e.g., flow rates, mean flow rates, velocities of one or more particles in one or more fluid flows, distributions of particle velocities in fluid flows) in the environment based on one or more properties of detected time-varying patterns of constructive and destructive interference detected using respective light-sensitive elements of the imager 714 of the device 700.

Some of the program instructions of the controller module 772 and the flow property determination module 774 may, in some examples, be stored in a computer-readable medium and executed by a processor located external to the device 700. For example, the device 700 could be configured to illuminate and to receive light from portion of biological tissue and then transmit related data to a remote server, which may include a mobile device, a personal computer, the cloud, or any other remote system, for further processing (e.g., for the determination of frequency content of the received light, for determining flow properties in the biological environment, for determining the location and other information about blood vessels or other structures of the biological environment based on the determined flow properties).

User interface 720 could include indicators, displays, buttons, touchscreens, head-mounted displays, displays of a console of a tele-surgical system, and/or other elements configured to present information about the device 700 to a user and/or to allow the user to operate the device 700. Additionally or alternatively, the device 700 could be configured to communicate with another system (e.g., a cellphone, a tablet, a computer, a remote server) and to present elements of a user interface using the remote system. The user interface 720 could be disposed proximate to the light source 712, imager 714, or other elements of the device 700 or could be disposed away from other elements of the device 700 and could further be in wired or wireless communication with the other elements of the device 700. The user interface 720 could be configured to allow a user to specify some operation, function, or property of operation of the device 700. The user interface 720 could be configured to present information about a biological tissue or other contents of a surgical environment (e.g., a map of vasculature, a presence of a target tissue) to the user using a display, to present a degree of progress of an ongoing function of the device 700 (e.g., a degree of progress in ablating a target tissue using a laser of the device 700), to present an image of a biological tissue or other environment, or to present some other information to a user. Other configurations and methods of operation of a user interface 720 are anticipated.

Communication system(s) 730 may also be operated by instructions within the program instructions 770, such as instructions for sending and/or receiving information via a wireless antenna, which may be disposed on or in the device 700. The communication system(s) 730 can optionally include one or more oscillators, mixers, frequency injectors, etc. to modulate and/or demodulate information on a carrier frequency to be transmitted and/or received by the antenna. In some examples, the device 700 is configured to indicate an output from the controller 710 by transmitting an electromagnetic or other wireless signal according to one or more wireless communications standards (e.g., Bluetooth, WiFi, IRdA, ZigBee, WiMAX, LTE). In some examples, the communication system(s) 730 could include one or more wired communications interfaces and the device 700 could be configured to indicate an output from the controller 710 by operating the one or more wired communications interfaces according to one or more wired communications standards (e.g., USB, FireWire, Ethernet, RS-232).

The computer readable data storage 760 may further contain other data or information, such as scattering, absorption, or other optical properties of tissues of a user of the device 700, that may be useful in determining flow properties. Further, the computer readable data storage 760 may contain data corresponding to certain tissue optical or other property baselines that describe expected optical or other properties of biological tissues. The baselines may be pre-stored on the computer readable data storage 760, may be transmitted from a remote source, such as a remote server, or may be generated by the flow property determination module 774 itself. The flow property determination module 774 may include instructions for generating individual baselines for the user of the device 700 based on data collected over a certain number of measurement periods. For example, the flow property determination module 774 may generate a baseline tissue scattering and/or absorption spectrum based on detected time-varying patterns of constructive and destructive interference in light received from portions of a biological tissue (e.g., from portions proximate to a portion of vasculature that has been determined and/or that has been indicated, e.g., by a surgeon, to be on the surface of the biological tissue), and store those baselines in the computer readable data storage 760 for later use (e.g., to determine a depth of a portion of vasculature within the biological tissue). Baselines may also be generated by a remote server and transmitted to the device 700 via communication system(s) 730.

In some examples, collected flow properties, maps of vasculature, or other information generated by the device 400 may additionally be input to a cloud network and be made available for download by a user's physician. Analyses may also be performed on the collected data, such as estimates of post-surgical recovery and/or determinations of post-surgical treatment or rehabilitation regimens, in the cloud computing network and be made available for download by physicians or clinicians. Further, collected information from individuals or populations of device users may be used by physicians or clinicians in monitoring efficacy of a surgical intervention or other treatment.

Figure 8A:
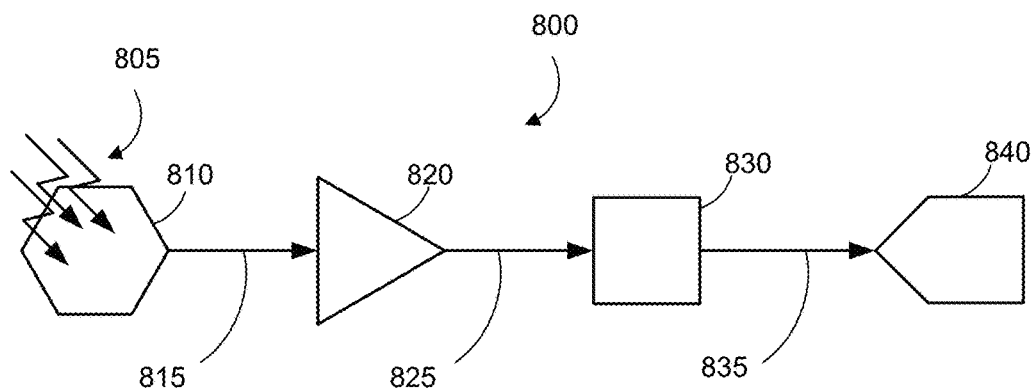
FIG. 8A is a functional block diagram of an example signal processing circuit.
Figure 8B:
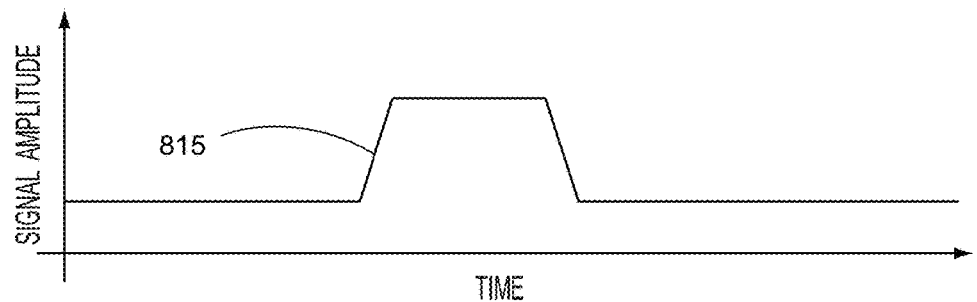
FIG. 8B is an example signal generated by the example signal processing circuit illustrated in FIG. 8A.

FIG. 8A is a functional block diagram of components that could be included in analog frontend circuitry as described herein (e.g., analog frontend circuitry that could be a part of the detection system 710 or of other devices described herein, e.g., 100, 300, 400). The example analog frontend circuitry 800 illustrated in FIG. 8A includes a light-sensitive element 810 of an imager configured to detect a time-varying pattern of constructive and destructive interference in received light 805 that is emitted from a corresponding portion an environment of interest (i.e., a portion corresponding to the particular light-sensitive element 810 of the imager) in response to illumination by a beam of coherent light. The light sensor output 815 is a signal related to the intensity of the received light 805. FIG. 8B illustrates an example waveform of the light sensor output 815 that includes a trapezoidal pulse corresponding to a speckle event. One or more properties of the trapezoidal pulse (e.g., a pulse width, a rise time, a rise rate, a fall time, a fall rate) could be related to a velocity of one or more scatterers in the environment of interest and/or to some other flow properties in the environment of interest.

Figure 8C:
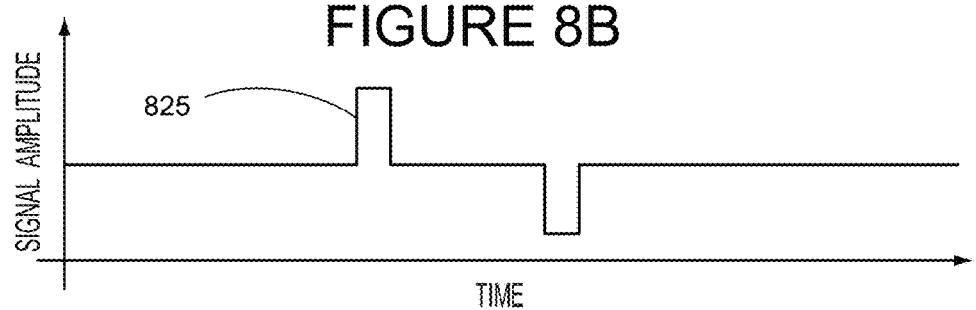
FIG. 8C is an example signal generated by the example signal processing circuit illustrated in FIG. 8A.

The example analog frontend circuitry 800 additionally includes a differentiator 820 configured to output a differentiator output 825 related to a rate of change of the light sensor output 815. The differentiator could be passive (e.g., an RC and/or RL filter circuit), active (e.g., an op-amp configured with capacitors, resistors, and/or other elements as a differentiator), or some combination thereof. Further, the differentiator output 825 could be related to the rate of change of the light sensor output 815; for example, the differentiator 820 could output a low-passed, rectified, or otherwise altered version of the rate of change of the light sensor output 815. FIG. 8C illustrates an example waveform of the differentiator output 825 corresponding to the trapezoidal pulse in the example light sensor output 815 waveform illustrated in FIG. 8B. The example waveform in FIG. 8C includes a first pulse having an amplitude related to a rise rate of the trapezoidal pulse illustrated in FIG. 8B and a timing corresponding to the rising edge of the trapezoidal pulse. The example waveform in FIG. 8C additionally includes a second pulse having an amplitude related to a fall rate of the trapezoidal pulse illustrated in FIG. 8B and a timing corresponding to the falling edge of the trapezoidal pulse. Note that a differentiator output 825 waveform corresponding to the example trapezoidal pulse could have a different shape according to the configuration of the differentiator 820. For example, the differentiator 820 could be configured to output a signal corresponding to a rectified or otherwise filtered version of the light sensor output 815 and the example differentiator output 825 would be changed correspondingly (in this example, the first pulse in the example differentiator output 825 would be filtered (e.g., would have some larger, finite rise time/fall time, etc.) and would substantially lack to second pulse).

Figure 8D:
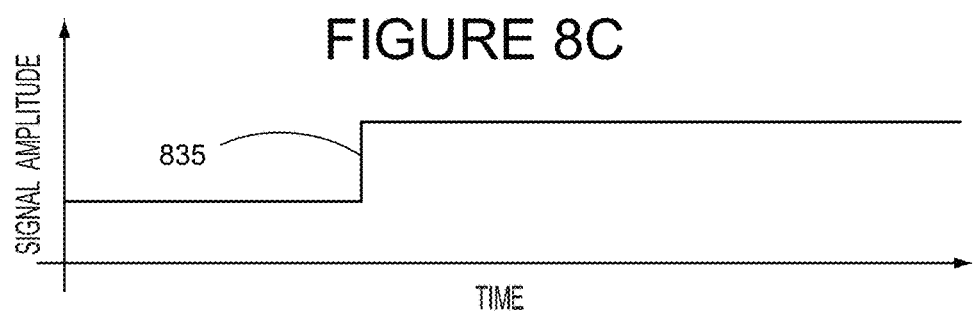
FIG. 8D is an example signal generated by the example signal processing circuit illustrated in FIG. 8A.

The example analog frontend circuitry 800 additionally includes a peak detector 830 configured to output a peak detector output 835 related to a maximum value of the differentiator output 825 during a specified previous time period. The peak detector 830 could include passive and active components configured in a variety of ways. In some examples, the peak detector 830 could include an op-amp, a rectifier, and a capacitor configured to output a peak detector output 835 corresponding to a maximum value of the differentiator output 825 in the past. The peak detector 830 could additionally include a reset electronic switch that could be operated to reset the peak detector 80, allowing the peak detector output 835 to correspond to a maximum value of the differentiator output 825 during a previous time period specified by the operation of the electronic switch. Additionally or alternatively, the peak detector 830 could include a lossy integrator. FIG. 8D illustrates an example waveform of the peak detector output 835 corresponding to the positive and negative pulses in the example differentiator output 825 waveform illustrated in FIG. 8C. The example waveform in FIG. 8D includes a positive step pulse having an amplitude corresponding to the amplitude of the first pulse illustrated in FIG. 8C and a timing corresponding to the rising edge of the first pulse. Note that a peak detector output 835 waveform corresponding to the example first and second pulses could have a different shape according to the configuration of the peak detector 830. For example, the peak detector 830 could include a lossy integrator, and the example peak detector output 835 would be changed correspondingly (in this example, the step response would decay to lower signal levels over time). In another example, the peak detector 830 could include an electronic switch operated to periodically reset the peak detector 830, and the example peak detector output 835 would be changed correspondingly (in this example, the step response would be replaced with a pulse having a duration corresponding to a difference in time between the timing of the first pulse of the example differentiator output 825 and the timing of a subsequent operation of the electronic switch).

The peak detector output 835 could form the output of the example analog frontend circuitry 800, and could be used to determine flow properties in the environment. As illustrated in FIG. 8A, an analog-to digital (ADC) converter 840 could be configured and operated to sample the peak detector output 835 at one or more points in time. For example, the ADC 840 could be operated by a microcontroller, and the microcontroller could use the output of the ADC 840 to determine flow properties in the environment of interest (e.g., the microcontroller could determine a flow rate of fluid in a particular portion of the environment corresponding to an amplitude of the peak detector output 835 measured using the ADC 840).

VI. ILLUSTRATIVE METHODS

Figure 9:
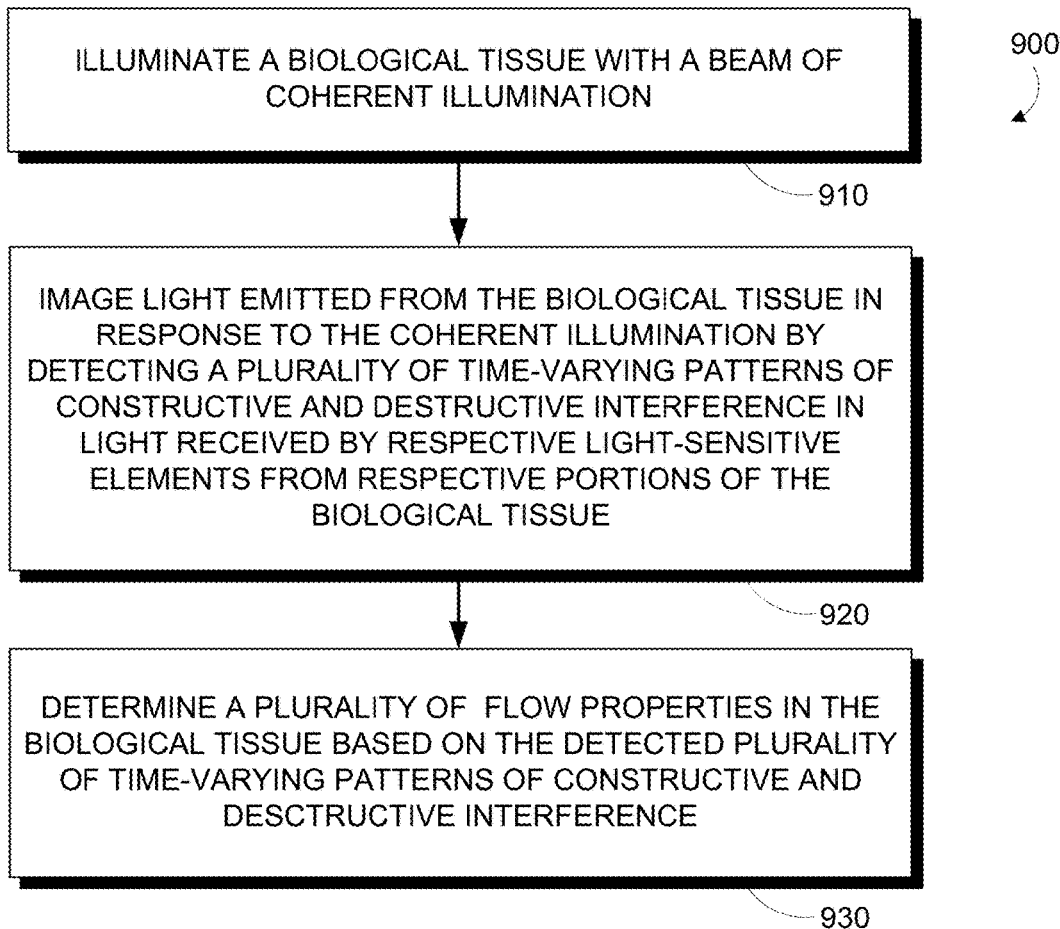
FIG. 9 is a flow chart of an example method.

FIG. 9 is a flowchart of a method 900 for measuring flow properties in a biological tissue using an imager. The imager includes a plurality of light-sensitive elements configured to detect time-varying patterns of constructive and destructive interference in light received from respective portions of the biological tissue in response to illumination of the biological tissue by a beam of coherent illumination.

The method 900 includes illuminating the biological tissue with a beam of coherent illumination (910). This could include operating a laser to emit the beam of coherent illumination. The coherent illumination is such that scatterers and other elements in the biological tissue scatter the coherent illumination such that light is responsively emitted from the biological tissue having time-varying patterns of constructive and destructive interference that are related at least to the configuration of the scatterers in fluid flows (e.g., blood flows, interstitial fluid flows) within the biological tissue. As such, the patterns of constructive and destructive interference could have a time-dependence related to flow properties in the biological tissue (e.g., a flow rate of fluid flow in a particular portion of the biological tissue). This can include emitting coherent illumination having a specific wavelength or coherence length, such that the coherent illumination can be scattered by scatterers disposed in the biological tissue, efficiently transmitted through the biological tissue, or other considerations. Illuminating the biological tissue with coherent illumination 910 can include emitting coherent illumination having a specified intensity, wavelength, coherence length, spectral line width, polarization, or other property. Further, illuminating the biological tissue with coherent illumination 910 can include emitting coherent illumination having different properties at different points in time. For example, it could include emitting coherent illumination having a first intensity, wavelength, coherence length, spectral line width, polarization, or other property at a first point in time and emitting coherent illumination having a second intensity, wavelength, coherence length, spectral line width, polarization, or other property at a second point in time.

The method 900 additionally includes imaging light emitted from the biological tissue in response to the coherent illumination by detecting a plurality of time-varying patterns of constructive and destructive interference in light received by respective light-sensitive elements of the imager from respective portions of the biological tissue (920). This can include detecting the intensity, wavelength, degree of polarization, orientation of polarization, or other properties of the light emitted from a particular portion of the biological tissue using a corresponding particular light-sensitive element of the imager. This can include detecting such properties at plurality of points in time and/or during a plurality of periods of time. Such periods of time could have one or more specified properties (e.g., a sample rate, an exposure time).

The method 900 additionally includes determining a plurality of flow properties in the biological tissue based on the plurality of time-varying patterns of constructive and destructive interference detected by the imager (930). This could include determining one or more flow rates, average flow rates, variances of flow rates, scatterer velocities, distributions of scatterer velocities, or some other flow property or properties. This could include determining one or more flow properties for a plurality of areas of the biological tissue, for a plurality of volumes within the biological tissue, or according to some other area- or volume-sampling or partitioning of the biological tissue.

Determining a plurality of flow properties in the biological tissue (930) could include sampling an output of one or more light-sensitive elements of the imager (e.g., an output related to an intensity of light, a polarization of the light, or some other property or properties of a detected time-varying pattern of constructive and destructive interference in received light) at a high frequency and then performing some calculation on the sampled output (e.g., determining a rate of amplitude change, a number of speckle events, a temporal property (e.g., duration, rise time) of speckle events, a frequency content, a frequency component) to determine one or more flow properties. Additionally or alternatively, electronics (e.g., analog frontend circuitry) of the wearable device could be configured to filter, modify, rectify, or otherwise perform analog operations on an output of the imager (e.g., an output of a light-sensitive element of the imager) to produce an output electronic signal that is related to flow properties in the biological tissue. Determining flow properties in the biological tissue (930) could include sampling the output electronic signal and then performing some calculation on the sampled output electronic signal to determine the flow properties. Additional or alternative embodiments and/or steps of determining flow properties in a biological tissue (930) are anticipated as described herein or otherwise.

The method 900 could include additional steps or elements in addition to illuminating the biological tissue (910), imaging light responsively emitted from the biological tissue (930), and determining a plurality of flow properties in the biological tissue (930). For example, the method 900 could include determining a map of vasculature in the biological tissue based on determined flow properties in the tissue. The method 900 could include indicating a determined map of vasculature or other determined information (e.g., flow properties) to a user using a user interface. The method 900 could include determining a depth of a portion of vasculature or other structure(s) in the biological tissue based on the detected time-varying patterns of constructive and destructive interference as described elsewhere herein. The method 900 could include determining a level of blood cell oxygenation in particular portions of the biological tissue by, e.g., illuminating the biological tissue with beams of coherent illumination at two or more different wavelengths and detected properties of light emitted from the biological tissue responsive to illumination by the two or more beams of coherent illumination. The method 900 could include introducing scatterers into the biological tissue (e.g., injecting, ingesting, transdermally transferring, or otherwise introducing the scatterers into a lumen of vasculature of a human). The method could include operating a robotic surgical system based on determined flow properties in the biological tissue. Additional and/or alternative steps of the method 900 are anticipated.

VII. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, a surgical intervention performed on the user, a scan, map, or other information about tissues of the user, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect a plurality of flow properties of biological tissues of a human body, it is noted that the disclosed devices, systems, and methods can be applied in other contexts as well. For example, detection systems configured to detect a plurality of flow properties of fluid in an environment using coherent light emitters and light sensors as disclosed herein may be included in wearable (e.g., body-mountable) and/or implantable devices. In some contexts, such a detection system is situated to be substantially encapsulated by bio-compatible polymeric material suitable for being in contact with bodily fluids and/or for being implanted. In some examples, such detection systems could be incorporated as part of a robotic surgical system, operated in combination with some other means or method for imaging and/or detecting some other information about biological tissues, or configured and/or operated as part of or in combination with some other system(s).

In other examples, devices, systems, and methods disclosed herein may be applied to measure flow properties of one or more fluids that are not in or on a human body. For example, detection systems disclosed herein may be included devices used to measure flow properties in a fluid of an animal. In another example, devices, systems, and methods disclosed herein may be applied to measure flow properties of an environmental fluid, such as a fluid in a river, lake, marsh, reservoir, water supply, sanitary sewer system, storm sewer system, or the atmosphere. In another example, devices, systems, and methods disclosed herein may be applied to measure flow properties of a fluid that is part of a process, such as a waste treatment process, industrial process, pharmaceutical synthesis process, food preparation process, fermentation process, a microfluidic laboratory or scientific process, or medical treatment process.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
a first light source;
an imager including a plurality of photodetectors; and
a controller coupled to the imager and the first light source, wherein the controller includes one or more integrated circuits with associated logic that when executed by the controller configures the controller to perform operations including:
emitting a first beam of coherent illumination from the first light source into a biological tissue, wherein the emitted first beam is scattered by the biological tissue to form scattered light, wherein an intensity of the scattered light changes in response to a plurality of speckle events, and wherein each of the plurality of speckle events corresponds to a time-varying pattern of constructive and destructive interference;
detecting the plurality of speckle events by sensing the intensity of the scattered light with the imager;
identifying at least one of a rising edge, a plateau, or a falling edge of the intensity of the scattered light with respect to time for each of the plurality of speckle events; and
determining a plurality of flow properties in the biological tissue based on at least one of the rising edge, the plateau, or the falling edge of the plurality of speckle events.

2. The system of claim 1, wherein the plurality of flow properties includes a plurality of flow rates of blood cells in the biological tissue.

3. The system of claim 2, wherein the plurality of flow properties includes at least one of a direction or an acceleration of the blood cells in the biological tissue.

4. The system of claim 1, wherein the operations further comprise:
determining that one or more portions of the biological tissue includes vasculature based at least on the plurality of flow properties in the biological tissue; and
determining a depth of the vasculature within the biological tissue based on the rising edge, the plateau, or the falling edge of the plurality of speckle events.

5. The system of claim 1, wherein the operations further comprise:
detecting a tumor in the biological tissue based at least on the plurality of flow properties in the biological tissue.

6. The system of claim 1, wherein the first beam of coherent illumination emitted from the first light source has a first wavelength between 400 nanometers and 1000 nanometers.

7. The system of claim 1, wherein the first beam of coherent illumination is polarized in a first direction, and wherein the imager further includes a polarization filter, wherein the polarization filter prevents the intensity of a first portion of the scattered light from being sensed by the imager, and wherein a polarization of the first portion of the scattered light is in the first direction.

8. The system of claim 1, wherein each of the plurality of photodetectors included in the imager are configured to receive individual portions of the scattered light that corresponds to a respective sub-region of the biological tissue.

9. The system of claim 8, wherein the controller further includes an analog frontend, wherein the analog frontend is configured to perform analog operations on an electronic output of a particular photodetector included in the plurality of photodetectors to produce an output electronic signal, wherein a property of the output electronic signal is related to a particular flow property included in the plurality of flow properties of the respective sub-region of the biological tissue, and wherein the controller determining the plurality of flow properties in the biological tissue includes determining the flow property of the respective sub-region of the biological tissue based on the output electronic signal of the analog frontend.

10. The system of claim 8, wherein the controller includes an analog-to-digital converter (ADC), and wherein the operations the controller is configured to perform further include:
sampling an output of a particular photodetector included in the plurality of photodetectors with the ADC at a rate greater than 1 megahertz.

11. The system of claim 1, wherein the first beam of coherent illumination emitted by the first light source has a first specified wavelength, wherein the system further includes a second light source, and wherein the operations the controller is configured to perform further include:
emitting a second beam of coherent illumination from the second light source into the biological tissue, wherein the second beam of coherent illumination has a second specified wavelength that is different from the first specified wavelength; and determining a level of blood cell oxygenation in a particular portion of the biological tissue based at least on a property of the scattered light from the particular portion of the biological tissue and a property of a second light scattered by the particular portion of biological tissue in response to the second beam of coherent illumination.

12. The system of claim 1, wherein determining the plurality of flow properties further includes:
   determining a velocity of a blood cell in the biological tissue based on a duration of the identified rising edge for a corresponding speckle event in the plurality of speckle events.

13. The system of claim 1, wherein determining the plurality of flow properties further includes:
   determining a distribution of velocities of blood cells in the biological tissue based on a duration of the identified rising edge in each of the plurality of speckle events.

14. The system of claim 1, wherein the imager further includes a color filter configured to block wavelengths of electromagnetic radiation different from a first wavelength of the first beam of coherent illumination.

* * * * *